United States Patent [19]

Atalar et al.

[11] Patent Number: 5,699,801
[45] Date of Patent: Dec. 23, 1997

[54] METHOD OF INTERNAL MAGNETIC RESONANCE IMAGING AND SPECTROSCOPIC ANALYSIS AND ASSOCIATED APPARATUS

[75] Inventors: Ergin Atalar; Paul A. Bottomley, both of Columbia; Elias A. Zerhouni, Baltimore, all of Md.

[73] Assignee: The Johns Hopkins University, Baltimore, Md.

[21] Appl. No.: 457,833

[22] Filed: Jun. 1, 1995

[51] Int. Cl.$^6$ ................................................ A61B 5/055
[52] U.S. Cl. .......................... 128/653.2; 128/653.5; 324/318; 324/322
[58] Field of Search ................ 128/653.2, 653.5, 128/653.1; 324/307, 309, 318, 322

[56] References Cited

U.S. PATENT DOCUMENTS

| | | | |
|---|---|---|---|
| 4,672,972 | 6/1987 | Berke | 128/653 |
| 4,766,381 | 8/1988 | Conturo et al. | 324/309 |
| 4,932,411 | 6/1990 | Fritschy et al. | 128/653 A |
| 5,170,789 | 12/1992 | Narayan et al. | 128/653.5 |
| 5,271,400 | 12/1993 | Dumoulin et al. | 128/653.2 |
| 5,293,872 | 3/1994 | Alfano et al. | 128/664 |
| 5,307,808 | 5/1994 | Dumoulin et al. | 128/653.2 |
| 5,473,251 | 12/1995 | Mori | 128/653.5 |

FOREIGN PATENT DOCUMENTS 0469035   2/1994   European Pat. Off. .

OTHER PUBLICATIONS

Kantor et al., "In vivo P Nuclear Magnetic Resonance Measurements in Cacine Heart Using a Catheter–Coil," Circulation Research, vol. 55, pp. 261, 266 (Aug. 1984).

Edelstein et al., "Electronic Decoupling of Surface–Coil Receivers for NMR Imaging and Spectroscopy," Journal of Magnetic Resonance, vol. 67, pp. 156–161 (1986).

Merickel et al., "Identification and 3–d Quantification of Atherosclerosis Using Magnetic Resonance Imaging," Comput. Biol. Med., vol. 18, pp. 89–102 (1988).

Martin et al., "Inflatable Surface Coil for MR Imaging of the Prostate", Radiology, Apr. 1988, pp. 260–270.

(List continued on next page.)

*Primary Examiner*—Ruth S. Smith
*Attorney, Agent, or Firm*—Arnold B. Silverman; Eckert Seamans Cherin & Mellott, LLC

[57] ABSTRACT

The invention provides a method for magnetic resonance imaging and spectroscopic analysis of the interior of a specimen which includes positioning the specimen within a main magnetic field, introducing an invasive probe having an elongated receiver coil into or adjacent to the specimen with the coil having at least one pair of elongated electrical conductors, preferably, generally parallel to each other disposed within a dielectric material and having a pair of ends electrically connected to each other. RF pulses are provided to the region of interest to excite magnetic resonance signals, gradient magnetic pulses are applied to the region of interest with the receiver coil receiving magnetic resonance signals and emitting responsive output signals which may be processed by a computer to provide image information for display in a desired manner. The method in a preferred form involves employing a flexible receiver coil which has uniform sensitivity along the coil and may be operated even when the magnetic resonance signal is in an oblique position. Tuning capacitance may be distributed along the length of the coil and/or a Faraday screen provided to minimize dielectric losses between the coil and the surrounding material of the specimen. The method may be used on a wide variety of specimens and in a preferred use is introduced into small blood vessels of a patient to facilitate determination of atherosclerotic plaque. Medical intervention procedures, such as plaque removal, may be employed generally simultaneously with the imaging of the present invention. Corresponding apparatus is provided.

85 Claims, 10 Drawing Sheets

OTHER PUBLICATIONS

Maynor et al., "Chemical Shift Imaging of Atherosclerosis at 7.0 Tesla," Investigative Radiology, vol. 24, pp. 52–60 (1989).

Mohiaddin et al., "Chemical Shift Magnetic Resonance Imaging of Human Atheroma," Br. Heart J., vol. 62, pp. 81–89 (1989).

Asdente et al., "Evaluation of Atherosclerotic Lesions Using NMR Microimaging," Atherosclerosis, vol. 80, pp. 243–253 (1990).

Pearlman et al., "Nuclear Magnetic Resonance Microscopy of Atheroma in Human Coronary Arteries," Angiology, vol. 42, pp. 726–733 (1991).

Vinitski et al., "Magnetic Resonance Chemical Shift Imaging and Spectroscopy of Atherosclerotic Plaque," Investigative Radiology, vol. 26, pp. 703–714 (1991).

Waller et al., "Intravascular Ultrasound: A Histological Study of Vessel During Life," Circulation, vol. 85, pp. 2305–2310 (1992).

Martin et al., "MR Imaging of Blood Vessel with an Intravascular Coil," J. Magn. Reson. Imaging, vol. 2, pp. 421–429 (1992).

Hurst et al., "Intravascular (Catheter) NMR Receiver Probe: Preliminary Design Analysis and Application to Canine Iliofemoral Imaging," Magn. Reson, Med., vol. 24, pp. 343–357 (Apr. 1992).

Dumoulin et al., "Real–time Position Monitoring of Invasive Devices Using Magnetic Resonance," Magnetic Resonance in Medicine, vol. 29, pp. 411–415 (Mar. 1993).

Spears et al., "In Vivo Coronary Angioscopy," Journal of the American College of Cardiology, vol. 1, No. 5, pp. 1311–1314 (1983).

Koechli et al., "Catheters and Guide Wires for Use in an Echo–Planar MR Fluoroscopy System," R. 79th Scientific Meeting, editor, Radiology, vol. 189 (P), p. 319 (Nov. 1993).

Abstract, McDonald et al., "Performance Comparison of Several Coil Geometries for Use in Catheters," R. 79th Scientific Meeting, editor, Radiology, vol. 189(P) p. 319 (Nov. 1993).

Merickel et al., "Noninvasive Quantitative Evaluation of Atherosclerosis Using MRI and Image Analysis," Arteriosclerosis and Thrombosis, vol. 13, pp. 1180–1186 (1993).

Yuan et al., "Techniques for High–Resolution MR Imaging of Atherosclerotic Plaques," J. Magnetic Resonance Imaging, vol. 4, pp. 43–49 (1994).

Martin et al., "Intravascular MR Imaging in a Porcine Animal Model," Magn. Reson, Med. vol. 32, pp. 224–229 (Aug. 1994).

METHOD OF INTERNAL MAGNETIC RESONANCE IMAGING AND SPECTROSCOPIC ANALYSIS AND ASSOCIATED APPARATUS

BACKGROUND OF THE INVENTION

1. Field of the Invention

The present invention relates to an improved system for magnetic resonance imaging and spectroscopic analysis of a wide variety of specimens and is in one embodiment employable with small blood vessels in determining the presence of atherosclerotic plaque and the composition thereof.

2. Description of the Prior Art

The advantageous use of magnetic resonance technology in providing safe, rapid images of a patient has long been known. It has also been known to employ magnetic resonance technology in producing chemical shift spectra to provide information regarding the chemical content of a material.

In a general sense, magnetic resonance imaging involves providing bursts of radio frequency energy on a specimen positioned within a main magnetic field in order to induce responsive emission of magnetic radiation from the hydrogen nuclei or other nuclei. The emitted signal may be detected in such a manner as to provide information as to the intensity of the response and the spatial original of the nuclei emitting the responsive magnetic resonance signal. In general, imaging may be performed in a slice or plane or multiple planes or three-dimensional volume with information corresponding to the responsively emitted magnetic radiation being received by a computer which stores the information in the form of numbers corresponding to the intensity of the signal. The pixel value may be established in the computer by employing Fourier Transformation which converts the signal amplitude as a function of time to signal amplitude as a function of frequency. The signals may be stored in the computer and may be delivered with or without enhancement to a video screen display, such as a cathode-ray tube, for example, wherein the image created by the computer output will be presented through black and white presentations varying in intensity or color presentations varying in hue and intensity. See, generally, U.S. Pat. No. 4,766,381.

U.S. Pat. No. 5,170,789 discloses an MR coil probe that is said to be insertable within a specimen, which has an opening, for purposes of nuclear magnetic resonance spectroscopy. It also discloses the use of a probe in the nature of an endoscope. The two component probe has a portion which is insertable into the body cavity and an external portion. As the tuning and matching circuit is outside the body, this limits the permitted extent of insertion into the body. Also, the body has an elliptical or circular shape that may deform during insertion and, as a result, require that the coil be tuned after insertion. If the coil were made of a very rigid material, insertion problems would also occur. A further limitation of this disclosure is that the coil axis cannot be placed along the z axis, i.e., the direction of the main magnetic field, otherwise, it would have a practically zero sensitivity. Finally, the coil has no receive only mode and, as a result, limits its application to spectroscopy. See, also, U.S. Pat. Nos. 4,932,411 and 4,672,972 which have the same inadequacies as the system in U.S. Pat. No. 5,170,789.

U.S. Pat. No. 4,932,411 discloses a solenoidal RF coil which is insertable into the body. The coil, while not disclosed in great detail, is generally similar to the coil of U.S. Pat. No. 5,170,789 except that a solenoidal coil is used instead of a single turn coil.

U.S. Pat. No. 4,672,972 discloses an NMR probe disposed at the distal end of a catheter or endoscope for obtaining NMR spectra from within a patient. The multi-turn probe has a parametric amplifier and/or a gate-array attached to it and also has a coil cooling system. The small parametric pre-amplifier and the gate-array could tend to create a significant amount of electrical noise to the received signal and, thereby, create a problem.

U.S. Pat. No. 5,271,400 discloses the use of an MR active specimen placed in an RF coil within a catheter. The frequency of the coil received signal provides information as to the position of the coil. It is not employed to provide MR imaging and spectroscopic analysis. U.S. Pat. No. 5,307,808 has a similar disclosure which employs the signal coming from the surrounding tissue.

One of the beneficial end uses of the present invention is in connection with atherosclerotic disease which is a major cause of mortality and morbidity in the United States. Localized forms of the disease, such as the deposit of plaque on the walls of blood vessels, can restrict local blood flow and require surgical intervention in some instances. While angiography is an effective means for detecting the luminal narrowing caused by plaque, it does not provide information regarding the nature of the process leading to blood flow reduction. Unfortunately, therapeutic methods, such as intravascular intervention, may experience failure partially due to the lack of valid animal models and lack of sufficiently precise imaging methods. An imaging system capable of providing detailed, qualitative and quantitative data regarding the status of vascular walls at the time of surgical intervention, could favorably influence the outcome by enabling the selection of the intervention method to be customized to the particular need. It would also serve to provide precise guidance for various forms of localized therapy. It has been known to use angioplasty and intravascular ultrasound for imaging plaques. See, generally, Spears et al., "In Vivo Coronary Angioscopy," Journal of the American College of Cardiology, Vol. 1, pp. 395–399 (May, 1993), and Waller et al., "Intravascular Ultrasound: A Histological Study of Vessel During Life," Circulation, Vol., 85, pp. 2305–2310 (1992). Intravascular ultrasound, however, provides several drawbacks, including the insensitivity to soft tissue and the inability to reliably detect thrombus and discriminate thrombus (new or organized) superimposed upon plaque from soft lipid-laden plaques. Also, the presence of artifacts related to transducer angle relative to the vessel wall, and an imaging plane limited to the aperture of the transducer in variable resolution at different depths of view are further problems with this approach.

The feasibility of identification of atherosclerotic lesions by employing MR microimaging in vitro has previously been suggested. See, for example, Pearlman et al., "Nuclear Magnetic Resonance Microscopy of Atheroma in Human Coronary Arteries," Angiology, Vol. 42, pp. 726–733 (1991); Asdente et al., "Evaluation of Atherosclerotic Lesions Using NMR Microimaging," Atherosclerosis, Vol. 80, pp. 243–253 (1990); and Merickel et al., "Identification and 3-d Quantification of Atherosclerosis Using Magnetic Resonance Imaging," Comput. Biol. Med., Vol. 18, pp. 89–102 (1988).

It has also been suggested that MRI can be used for quantification of atherosclerosis. See, generally, Merickel et al., "Noninvasive Quantitative Evaluation of Atherosclerosis Using MRI and Image Analysis," Arteriosclerosis and Thrombosis, Vol. 13, pp. 1180–1186 (1993).

Yuan et at, "Techniques for High-Resolution MR Imaging of Atherosclerotic Plaques," J. Magnetic Resonance Imaging, Vol. 4, pp. 43–49 (1994) discloses a fast spin echo MR imaging technique to image atherosclerotic plaques on an isolated vessel that has been removed by carotid endarterectomy. As the signal-to-noise ratio (SNR) decreases with the decrease in imaging time and increase in resolution, special RF receiver coils were designed. The article suggests that by the use of special MR hardware at 1.5T using various T1 and T2-weighted pulse sequences, it is possible to discriminate foam cells, fibrous plaque organized thrombus, new thrombus, loose necrosis and calcium.

It has also been suggested that the fat content of atherosclerotic plaque in excised tissue samples can be determined using chemical shift imaging or chemical shift spectroscopy. See, generally, Vinitski et al., "Magnetic Resonance Chemical Shift Imaging and Spectroscopy of Atherosclerotic Plaque," Investigative Radiology, Vol. 26, pp. 703–714 (1991), Maynor et al., "Chemical Shift Imaging of Atherosclerosis at 7.0 Tesla," Investigative Radiology, Vol. 24, pp. 52–60 (1989), and Mohiaddin et al., "Chemical Shift Magnetic Resonance Imaging of Human Atheroma," Br. Heart J., Vol. 62, pp. 81–89 (1989).

The foregoing prior art articles in the aggregate could lead one skilled in the art to conclude that MR, while having potential for fully characterizing vessel wall disease, suffers from low anatomic resolution unless used in vitro on small specimens with high resolution methods.

MR compatibility characteristics of various catheter and guide wire systems for use in interventional MR procedures, has been considered. See Dumoulin et al., "Real-time Position Monitoring of Invasive Devices Using Magnetic Resonance," Magnetic Resonance in Medicine, Vol. 29, pp. 411–415 (Mar. 1993) and Koechli et al., "Catheters and Guide Wires for Use in an Echo-Planar MR Fluoroscopy System," R. 79th Scientific Meeting, editor, Radiology, Vol. 189 (P), p. 319 (Nov. 1993). It is known that in order to obtain the desired high-resolution imaging and spectroscopy of arteriosclerotic plaques, a coil must be placed close to the target blood vessel.

In Kantor et al., "In vivo sip Nuclear Magnetic Resonance Measurements in Cacine Heart Using a Catheter-Coil," Circulation Research, Vol. 55, pp. 261–266 (Aug. 1984), there is disclosed an effort to improve the signal-to-noise ratio in the $^{31}P$ spectroscopy of a dog myocardium using an elliptical coil. This coil is rigid and rather bulky. Further, as it was designed for spectroscopy of the myocardium, it is not ideal for vessels.

Disclosures of efforts to develop catheter coils for imaging vessel walls are contained in Martin et al., "MR Imaging of Blood Vessel with an Intravascular Coil," J. Magn. Reson. Imaging, Vol. 2, pp. 421–429 (1992) and Hurst et al., "Intravascular (Catheter) NMR Receiver Probe: Preliminary Design Analysis and Application to Canine Iliofemoral Imaging," Magn. Reson. Med., Vol. 24, pp. 343–357 (Apr. 1992). These disclosures employ two tiny diameter, back-to-back solenoid coils to produce a good axial profile when the coils are placed along the main magnetic field. The magnetic fields detected by these coils is perpendicular to the long axis of the catheter.

Martin et al., "Intravascular MR Imaging in a Porcine Animal Model," Magn. Reson. Med., Vol. 32, pp. 224–229 (Aug. 1994) discloses use of the system disclosed in the above-cited Martin et al. article for high-resolution images of live animals. See, also, Abstract, McDonald et al., "Performance Comparison of Several Coil Geometries for Use in Catheters," R. 79th Scientific Meeting, editor, Radiology, Vol. 189(P) p. 319 (Nov. 1993). A strong disadvantage of these disclosures is that multislice acquisition cannot be carried out because the longitudinal coverage of the sensitive regions is limited to a few millimeters. Also, these designs require, in order to function effectively, that the long axis of the coils be parallel to the main magnetic field. Unfortunately, for most vessels of interest, such as coronary arteries or veins, for example, the vessels are tortuous and oblique to the magnetic field. Further, to the extent that the coil itself does not have desired flexibility while maintaining the desired efficiency of data acquisition, they are also unsuitable for the purposes of the present invention.

There remains, therefore, a very real and substantial need for an improved means for MR imaging and spectroscopic analysis of specimens in a manner which provides efficient data acquisition with maximum SNR while permitting in vivo or in vitro acquisition from small vessels, as well as other body openings and a wide range of other types of specimens.

SUMMARY OF THE INVENTION

As used herein, the term "specimen" shall refer to any object placed in the main magnetic field for imaging or spectroscopic analysis and shall expressly include, but not be limited to members of the animal kingdom, including humans, test specimens, such as biological tissue, for example, removed from such members of the animal kingdom and inanimate objects which may be imaged by magnetic resonance techniques or contain water or sources of other sensitive nuclei.

As used herein, the term "patient" shall mean human beings and other members of the animal kingdom.

The present invention has met the above described need.

The method of the present invention includes positioning a specimen within a main magnetic field, introducing an invasive probe having an elongated receiver coil into or adjacent to the specimen, imposing a main magnetic field on the region of interest of the specimen, applying RF pulses to the region of interest to excite magnetic resonance signals within the specimen, applying gradient magnetic pulses to the region of interest to spatially encode the magnetic resonance signals with a receiver coil receiving the magnetic resonance signals, and emitting output signals to computer means which convert them into image or spectra information which is provided to display means for display of a corresponding image or spectra.

The receiver coil employed in one preferred embodiment has at least one pair of elongated conductors which are preferably parallel to each other, disposed within a dielectric material, and having a pair of ends electrically connected to each other. The receiver coil for most embodiments is preferably flexible so as to permit efficient movement through or adjacent to the specimen openings and other specimens to be analyzed regardless of whether the path is straight or not. The coil is designed to have data acquisition capability substantially over all coil orientations relative to the main MR magnetic field, thereby permitting data acquisition even at oblique angles.

The coil is also adapted to be employed in chemical shift imaging through acquisition of spatially localized chemical shift information.

In this manner, the method enables both imaging and chemical shift analysis which may also be advantageously employed substantially simultaneously with surgical intervention.

The coil has substantial length and may be on the order of about 2 cm to 50 cm and may have a relatively small maximum outer dimension of about 0.5 mm to 2 cm.

In one embodiment the receiver coil also functions as a transmitting coil to provide the RF signals and, thereby, provide enhanced efficiency of operation for certain uses.

The method may also employ additional elements, such as a decoupling circuit, a Faraday shield, and a tuning/matching circuit in order to provide enhanced operation.

In a preferred embodiment, the coil may have more than two pairs of conductors with each conductor in a pair being electrically connected to the other and the additional pairs being angularly offset with respect to the first pair.

Corresponding apparatus is provided.

It is an object of the present invention to provide a method and apparatus for providing high-resolution and spectroscopic imaging of the interior of specimens, including in vivo and in vitro real-time imaging of patients and patient derived specimens.

It is a further object of the present invention to provide such a system which will permit rapid imaging of walls of small, tortuous blood vessels with high-resolution, as well as other specimens, and will permit the use of multislice data acquisition techniques.

It is a further object of the present invention to employ elongated, flexible coils in such a system to provide both qualitative and quantitative data and to facilitate use of the same substantially simultaneously with medical intervention to correct undesired conditions.

It is a further object of the present invention to provide such a system which facilitates acquiring morphological information about soft tissue and plaque.

It is a further object of the present invention to provide such a system which facilitates acquiring chemical information about soft tissue and plaque.

It is a further object of the present invention to provide such a system wherein the flexible coil may function only as a receiver coil or may function as a coil for both excitation and detection of MR signals.

It is a further object of the present invention to provide such a system wherein the coil may be placed within a catheter or secured to an endoscope, a biopsy needle, or other probe-type medical devices.

It is a further object of the present invention to provide such a system wherein no tuning of the system is required after insertion into a specimen.

It is a further object of the present invention to provides system having such a coil which is sensitive to magnetic resonance signals even in oblique positions and provides generally uniform sensitivity along the coil.

It is a further object of the invention to provide such a system which may be employed with conventional hardware.

These and other objects of the present invention will be more fully understood from the following description of the invention with reference to the illustration appended hereto.

DESCRIPTION OF THE PREFERRED EMBODIMENTS

Figure 1:
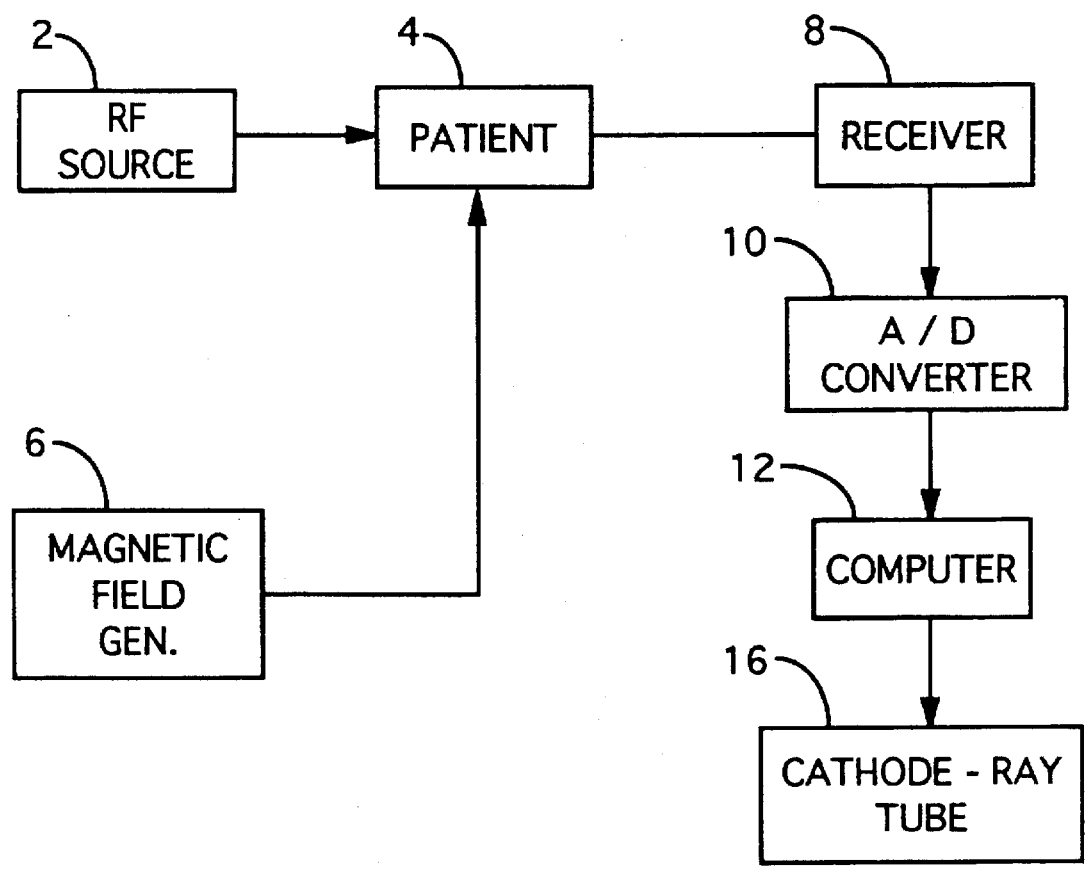
FIG. 1 is a schematic illustration of a magnetic resonance imaging system.

FIG. 1 shows a schematic representation of the general concept of magnetic resonance imaging as employed with a patient. An RF source 2 provides pulsed radio frequency energy to the specimen to excite MR signals therefrom which, in the form shown, is a patient 4 disposed in the main magnetic field which is created by a magnetic field generator 6. The specimen is generally aligned with the main magnetic field and the RF pulses are imposed perpendicular thereto. Where oblique imaging is employed, the angle of impingement of the vector representing the spatial gradient of the magnetic field will be angularly offset from either the x, y, or z directions. This arrangement results in excitation of the nuclei within the area or volume to be imaged and causes responsive emission of magnetic energy which is picked up by receiver 8.

The receiver 8 may be a coil which has a voltage induced in it as a result of such responsive emissions of magnetic energy. As a practical matter, separate coils or identical coils may be employed as the RF source 2 and receiver 8. The signal emerging from receiver 8 is amplified, phase-sensitive detected, and passes through analog-to-digital (A/D) convertor 10 and enters computer 12. Within computer the Fourier Transformations of signals convert the plot of amplitude versus time to a map of the distribution of frequencies by plotting amplitude versus frequency. The Fourier Transformations are performed in order to establish the intensity value locations of specific pixels and to obtain chemical shift spectra at those locations. These values may be stored, enhanced or otherwise processed, and emerge to be displayed on a suitable screen, such as a cathode-ray tube 16, for example.

Figure 2:
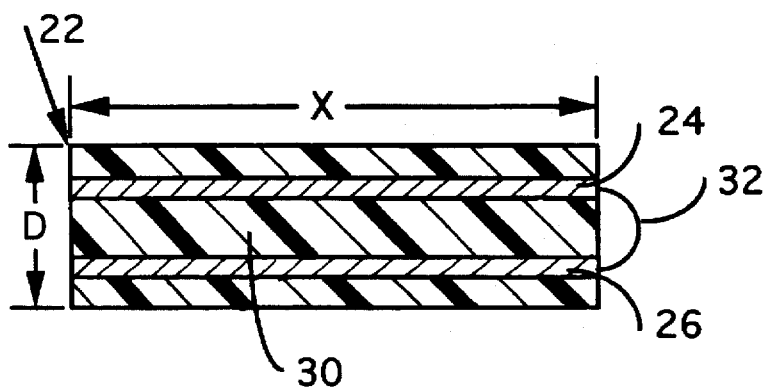
FIG. 2 is a cross-sectional illustration of a form of coil usable in the present invention.
Figure 3:
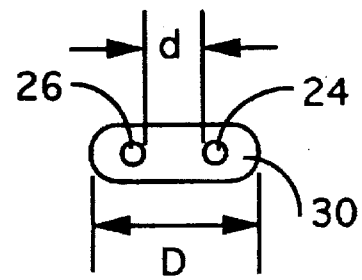
FIG. 3 is a left end view of the coil of FIG. 2.

Referring to FIGS. 2 and 3, there is shown a preferred form of coil 22 of the present invention. The coil 22 has a pair of electrodes 24, 26 which in the form shown, are generally parallel and spaced from each other a distance d which is about 0.1 mm to 30 mm and, preferably, about 0.1 mm to 10 mm. The coil 22 has a dielectric material 30 which serves to reduce dielectric losses of the coil 22 and of the specimen. Ends of conductors 24, 26 of the coil 22 are electrically connected by wire 32. The coil, as measured along the portion of the conductors 24, 26 contained within dielectric 30, has an overall length X which may be about 2 cm to 50 cm and, preferably about 5 cm to 20 cm. The coil has a width D which is the major dimension of about 0.5 mm to 2 cm and, preferably about 0.5 mm to 15 mm. The conductors 24, 26 may have an individual diameter of about 0.1 mm to 3 mm and, preferably about 0.1 mm to 1 mm. It is preferred that the separation d of the conductors 24, 26 be a dimension substantially less than the length X. The conductors 24, 26 are preferably made of a good electrical conductor, such as copper, silver, or aluminum, for example. Because of the skin effect, however, wherein only about an 8 μm outer layer of the conductor carries electrons at RF frequencies, a material plated with a good conductor will also function effectively. The dielectric material 30 should be resilient so as to permit flexing of the coil 22 and return to its original configuration. Any suitable dielectric material having the properties required to function in this environment may be employed. While the thickness of the dielectric will depend to an extent on the specific material selected, in general, it is preferred that the conductors 24, 26 be covered by at least 0.1 mm of dielectric material. A suitable dielectric may, for example, be a bio-compatible plastic material, or blend having the desired properties. The dielectric material employed may, for example, be tetrafluoroethylene, which is sold under the trade designation, "Teflon." It is known for its fine electrical insulating properties, does not interact with any components in water, and can be safely used in blood vessels.

It will be noted that as is shown in FIGS. 2 and 3, the dielectric 30 is, preferably, sufficiently rigid to resist undesired deformation involving significant alterations in the spacing d of the electrical conductors 24, 26 which, in the form shown, are impregnated therein. It resists deformation other than through resilient flexing of the entire coil 22.

With the coil shown in FIGS. 2 and 3, the inductance can be calculated by Formula 1.

$$L = \frac{Z_0}{w} \tan\frac{2\pi l}{\lambda} \quad (1)$$

wherein "L" equal inductance, "$Z_0$" is the characteristic impedance of the wire, and is a function of the separation and diameter of the conductors, the "w" is the larmor frequency in radians per second. For 1.5 Tesla, larmor frequency is approximately $4\times10^8$ radian/sec., "l" is the length of the cable, and $\lambda$ is the wavelength between the wires, which is approximately 1.5 meters with the coil inserted into a blood vessel.

Figure 4:
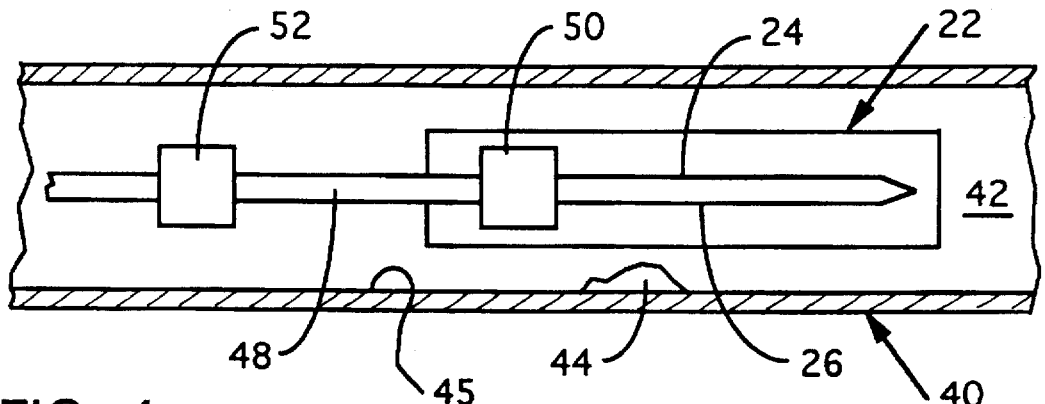
FIG. 4 is a fragmentary partially schematic illustration of the coil of FIG. 2 and associated electronic components positioned in a blood vessel.

In one method of employing the present invention in combination with a catheter to image or spectrographically analyze a blood vessel, a guide wire may first be inserted into the vessel. The motion of the guide wire can be observed by the method described in U.S. Pat. Nos. 5,271,400 or 5,307,808, or by any other suitable method. A catheter is then inserted into the vessel employing the guide wire. The guide wire is then removed and the catheter coil of the present invention is inserted. The catheter is then removed. This positions the coil within the vessel as shown in FIG. 4. If desired, other means of introducing the coil into the vessel may be employed.

Referring to FIG. 4, there is shown in cross-section of a blood vessel 40 having an interior bore 42 filled with blood (not shown). The blood vessel 40 has one or more atherosclerotic plaque deposits, such as plaque deposit 44 which is secured to the interior surface 45 of the vessel 40. The coil 22, in the form shown, is fully embedded within dielectric 30 with the connecting wire 32 also contained within the dielectric 30. The tuning/matching circuit 50 is also embedded in the dielectric material 30 and is electrically connected to the coil. A coaxial cable 48 is connected to the tuning/matching circuit 50 which will be described hereinafter in greater detail and serves to match impedance of coil 22 with the impedance of the coaxial cable 48. A de, coupling diode 52 is provided with coaxial cable 48.

Figure 5A:
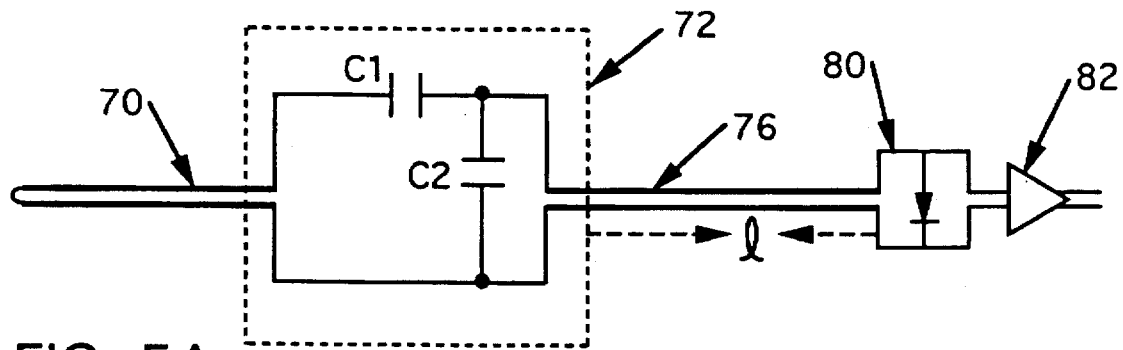
FIG. 5A is a circuit diagram of a catheter coil.

Referring to FIG. 5A, a specific example of the invention will be considered.

EXAMPLE 1

A coil 70 has two conductors similar to those shown in FIGS. 2 through 4 made of 30 AWG 7.5 cm conductor wire having a dielectric insulator made of Teflon with the conductors being silver-plated copper conductors shorted at one end. This was employed as the catheter coil. For tuning and matching at the time of manufacture, tuning/matching circuit 72 is provided with capacitors C1 and C2, which are electrically connected to the coil 70. The capacitors may be provided on a microchip having a dimension of about 1.5 mm×1.5 mm×1.4 mm, for example.

The other end of the tuning/matching circuit 72 is electrically connected to coaxial cable 76 which has a 2 mm outer diameter and a 50 ohm resistance and is used to carry the magnetic resonance signal from the coil to the processor (not shown in this view). If desired, a Teflon tape may be employed to cover both the coil 70 and the capacitor circuit 72.

In order to de, couple the transmit and the catheter coil, in the form shown, a PIN diode 80 is placed in the coaxial cable 76. The diode turns on during RF transmission using a DC current applied by the scanner hardware. If desired, other means of decoupling may be employed. The coaxial cable length "l" is precisely adjusted so that when the diode 80 is on, the coaxial cable 76 behaves like an inductor and resonates with capacitor C2 to disable a current through the receiver coil 70. In the decoupling circuit, in order to resist current induction in the receiver coil during RF transmission, the MR scanner may provide a positive DC pulse to the coil 70 for this purpose. This normally turns on PIN diode 80. When this PIN diode 80 is on, no current from the coil 70 is allowed to pass. This can be incorporated into the cathode coil probe assembly by placing the diode 80 as a shunt to a coaxial cable at a predetermined distance "l" from the tuning circuit 72. When the diode 80 is on, the coaxial cable behaves like an inductor and resonates with the parallel capacitor C2 that disables the induced current flow from the catheter coil 70. As it is desirable to put only a small number of electronic components in the vessel, a $\lambda/2$ cable length may be added to this length and the diode 80 located outside the blood vessel.

Figure 5B:
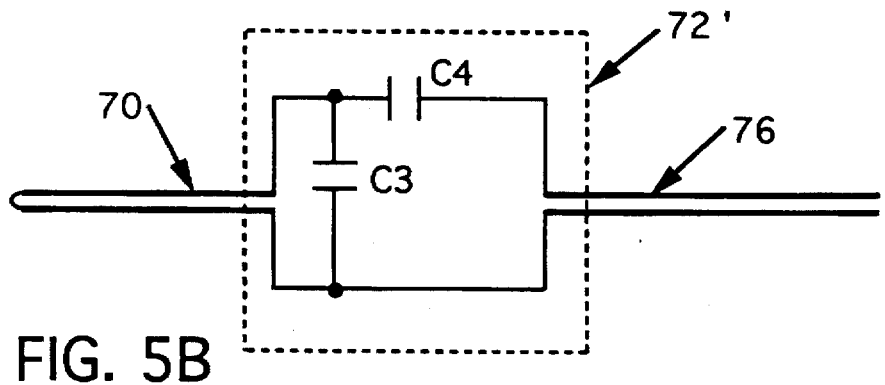
FIGS. 5B and 5C illustrate other suitable tuning and matching circuits.
Figure 5C:
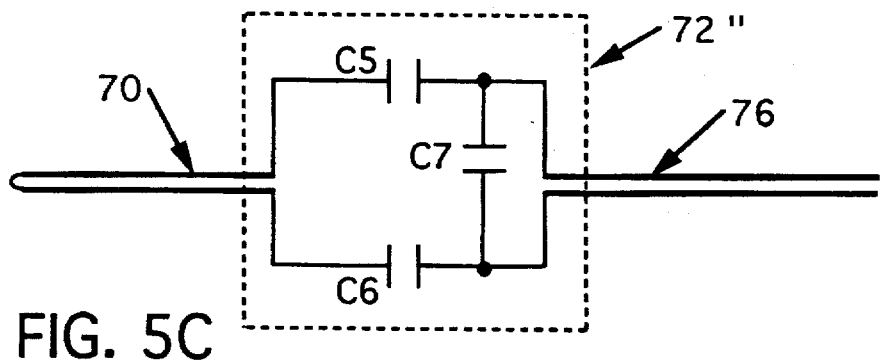

The tuning/matching circuit 72 maximizes RF power transfer from the receiver coil 70 to the preamplifier 82 as shown in FIG. 5A. Preamplifier 82 receives and amplifies the output of PIN diode 80. The tuning/matching circuit 72 is preferably placed next to the coil 70 to minimizes losses. In the catheter coil embodiment, it may be in the catheter closed end 42 (FIG. 4). The capacitors C1, C2 may be relatively small fixed capacitors whose values are chosen to resonate coil 70 at the MR frequency of the nuclei of interest and match the coil to the optimum input impedance of preamplifier 82. For example, if "f" is the MR resonance frequency, the coil may be tuned to resonate at f by adjusting the values of the capacitors C1 and C2 in FIG. 5A such that the condition $f=(2\pi\sqrt{[L\ C]})^{-1}$ is met, where L is the coil inductance with the coil in the sample, and C is the sum of the tuning capacitance, $Ct=C1\ C2/(C1+C2)$, and may stray capacitance along the length of the coil that may result from interactions between the coil conductor and the specimen in which it is inserted. Stray capacitance can be reduced by reducing the length of the coil 70. The value of capacitor C2 may be adjusted so that the impedance of the coil at resonance in the specimen, as viewed by the preamplifier 82, is optimally matched to maximize the signal-to-noise ratio of the preamplifier 82, for example, it may be adjusted to be 50 Ω at resonance. The arrangement of tuning/matching network 72 in FIG. 5A is not limiting and it will be understood that other tuning and matching arrangements will be evident to those skilled in the art, including those illustrated in FIGS. 5B and 5C. In FIGS. 5B and 5C, capacitor values C3, C4, and values C5, C6, C7, respectively, are adjusted to meet the same criteria so as to resonate the coil at the desired MR frequency, and to match the coil impedance at resonance to optimize the MR signal-to-noise ratio.

In another test, a specimen in the form of an aorta from the rabbit's left femoral artery was employed. The catheter coil 70 was inserted into aorta. An image with a 3 mm thickness, a field of view (FOV) of 50×25 mm and a 512×256 matrix, 4NEX, TR/TE 2000/50 ms was obtained using a fast spin echo pulse sequence. An image showing the two conductors and the vessel wall around the coil, as well as the structures around the vessel was visualized successfully.

In another experiment, an isolated dog heart was employed. The catheter coil was placed in the circumflex artery of the heart from the aorta. The isolated heart was placed in a saline solution. The orientation of the heart was adjusted so that the long axis of the coil was aligned with the main magnetic field (z direction). The axial images of the heart were obtained using fast spin echo imaging techniques. An image resolution of 100 μm×100 μm with a 3 mm slice thickness was obtained with a 4 NEX data acquisition. The vessel wall and myocardium were visualized in the image. When the coil was placed with the long axis orthogonal to the magnetic field, there remains sufficient x and y components of the coil's magnetic field to permit detection of a magnetic resonance signal.

Figure 6A:
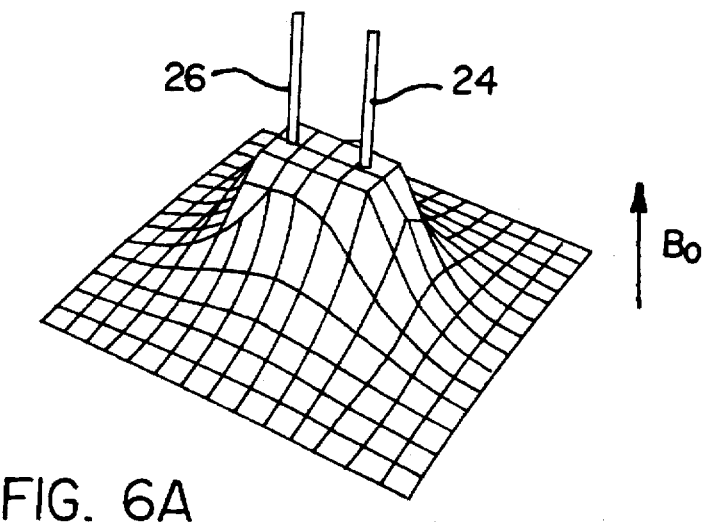
FIG. 6A is a sensitivity map of the catheter coil with the coil oriented parallel to main magnetic field $B_0$.
Figure 6B:
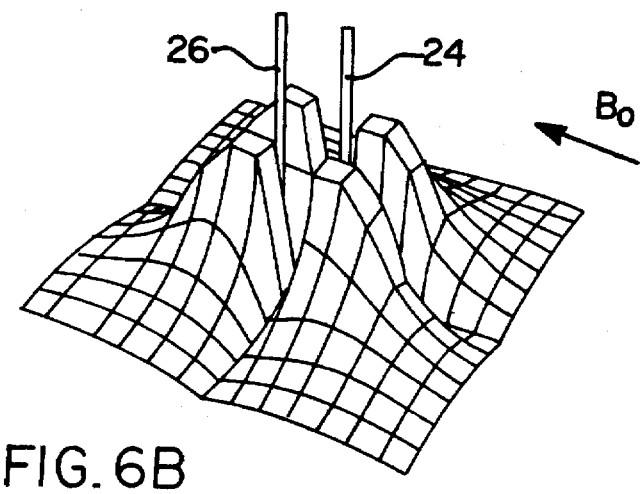
FIG. 6B is a sensitivity map of the catheter coil of FIG. 2 with the coil oriented perpendicular to the main magnetic field $B_0$.
Figure 6C:
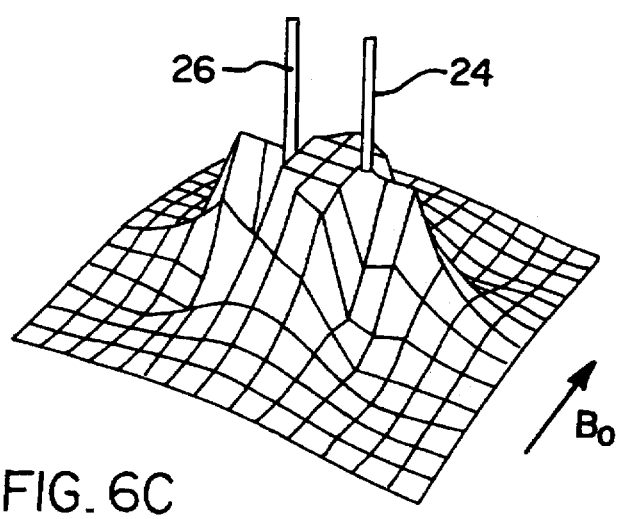
FIG. 6C is a sensitivity map of the coil of FIG. 2 with the coil positioned generally tangential to main magnetic field $B_0$.

Referring to FIGS. 6A, 6B and 6C, there is shown a sensitivity map or plot of the catheter coil. Assuming that the sensitive region in an axial field produced by the coil is much smaller than the coil length X (FIG. 2) and that the diameter of the conductors 24, 26 is much less than the separation "d" between conductors 24, 26, the RF field sensitivity of the coil 22 can be calculated from the Biot-Savart law with $\hat{z}$ as the direction of a magnetic field $\hat{B}_0$ and the net field perpendicular to $B_0$ is the transverse field. MR detection and excitation only involves the transverse field. In general, a catheter MR coil of the present invention may be oriented in any direction relative to $B_0$. The wires 24, 26 of the coil 22 are held at fixed separation "d" such that length X is much greater than d. The transverse field amplitude produced by the coil oriented in the 3 orthogonal Cartesian directions is shown in FIGS. 6A–6C. It is seen from these figures that the coil is insensitive to magnetic field changes along its long axis and produces a transverse field in any orientation with respect to the magnetic field, although its sensitivity profile varies with the orientation relative to the $B_0$ magnetic field. If the conductors 24, 26 are oriented in the same direction as the $B_0$ field as in FIG. 6A, the sensitivity is angularly uniform. Sensitivity generally drops approximately in proportion to 1/r along the radial axis where "r" is the distance from the center of the coil.

It is noted in FIG. 6B wherein the field $B_0$ is perpendicular to the coil that the transverse magnetic field map is altered, but data is still received. Finally, with respect to FIG. 6C, wherein the $B_0$ field is tangential to the coil, there is further modification of the map, but meaningful data is nevertheless obtained. As a result of this characteristic of coil 22, coil 22 may function effectively when the coil is not ideally located with respect to the main magnetic field $B_0$. Such would be the case in passing the coil through a tortuous path, such as in a small blood vessel.

A suitable MR scanner usable in the practice of the present invention is the G.E. 1.5T signa magnetic resonance scanner.

Figure 7:
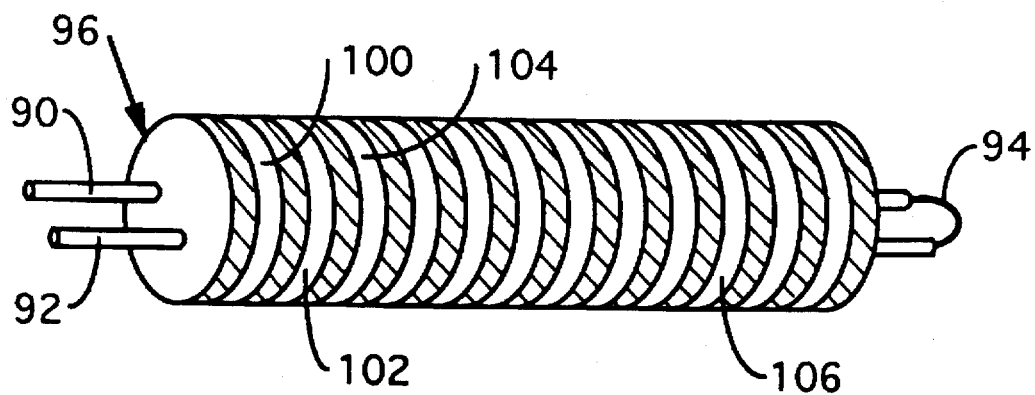
FIG. 7 is a perspective partially schematic view of the coil of FIG. 2 provided with a Faraday shield.

As a result of high dielectric losses resulting from interaction of the coil with the vascular environment, the quality factor (Q) of the coil may tend to drop as the length of the coil increases and, in addition, the tuning of the coil may be altered. In order to reduce the risk of such undesired dielectric losses and detuning effects, a Faraday shield may be employed. It serves to decrease the electric field and, therefore, the dielectric losses of the coil when in situ. As is shown in FIG. 7, a coil of the two-conductor type shown in FIG. 2, but with a cylindrical configuration, has a pair of generally parallel, straight conductors 90, 92 having a shunt 94 electrically connecting ends thereof, and having the conductors 90, 92 passing through a flexible dielectric material 96. The Faraday shield, in the form shown, consists of a plurality of rings, such as rings 100, 102, 104, 106, for example, which are positioned about the circumference of the dielectric material 96 and are axially spaced from each other. The rings 100, 102, 104, 106 may be continuous or discontinuous as by being a slit or annularly discontinuous.

Figure 8:
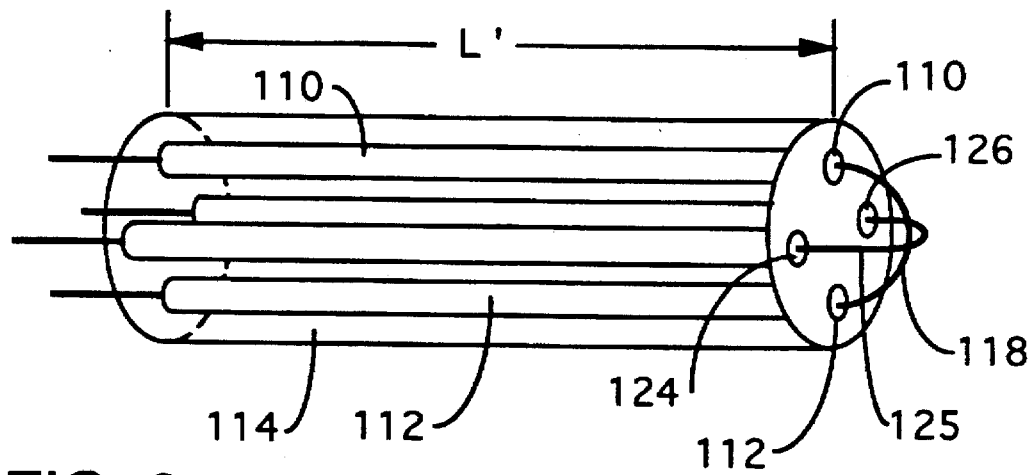
FIG. 8 is a modified form of coil of the present invention having two pairs of electrodes rather than the single pair electrode of the coil of FIG. 2.
Figure 9:
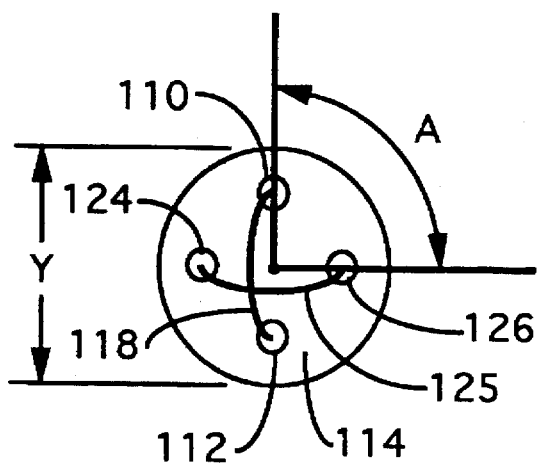
FIG. 9 is a left end view of the coil of FIG. 8 without the end connectors shown.
Figure 10A:
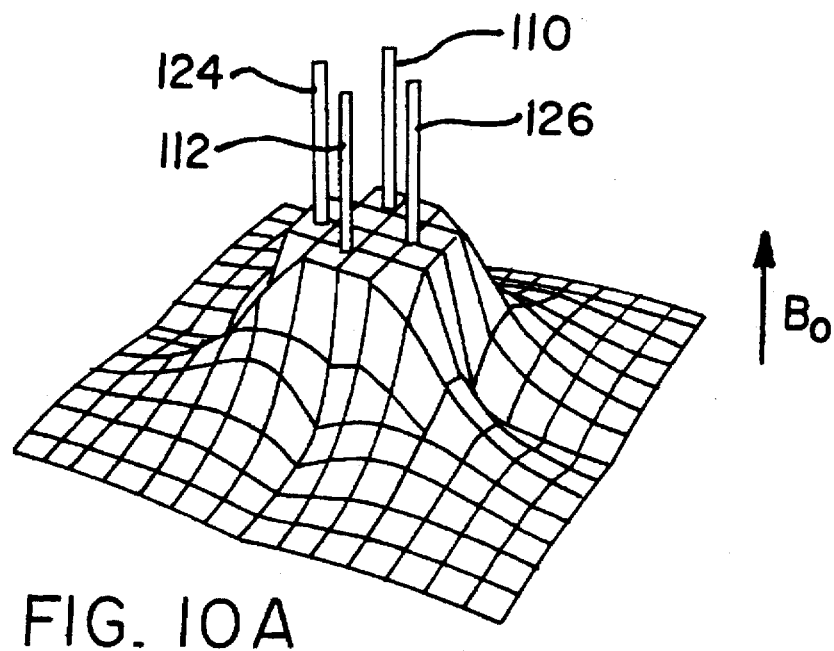
FIG. 10A is an MR signal sensitivity map of the coil of FIG. 8 with the coil oriented parallel to the magnetic field $B_0$.

Referring to FIGS. 8 and 9, a preferred form of coil of the present invention will be considered. This embodiment provides improved SNR and increased uniformity of sensitivity. This coil is generally similar to that of FIGS. 2 through 4, except that instead of having a single pair of conductors 24, 26, which are electrically connected to each other by a shunt 32, two pairs of electrical conductors which are positioned in planes orientated at 90° relative to each other are employed. In this embodiment, a first pair of conductors 110, 112 extends through a dielectric material 114 which, preferably, is generally flexible and encloses the conductors 110, 112. The ends of conductors 110, 112 are shunted by electrical connector 118. Similarly, a second pair of conductors 124, 126 are contained within the dielectric material 114 and are positioned 90° out of alignment with a plane passing through conductors 110, 112 as shown by angle A in FIG. 9. The ends of conductors 124, 126 are shunted by electrical connector 125. As shown in FIG. 10A, the transverse magnetic field map, when the main magnetic field $B_0$ is oriented generally parallel with the orientation of coils of conductors 110, 112, 124, 126 is somewhat similar to that of FIG. 6A, but offers the additional advantage of higher sensitivity. This embodiment is advantageous as compared with the two conductor coil with respect to improved uniformity in the vicinity of the conductors and the uniformity is less sensitive to coil orientation with respect to the main magnetic field $B_0$.

Figure 10B:
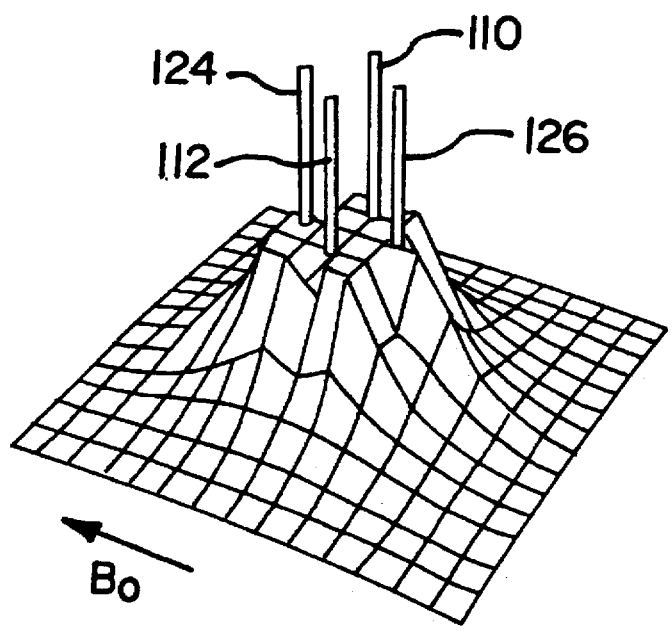
FIG. 10B is a sensitivity map of the coil of FIG. 8 with the coil oriented generally perpendicular to the magnetic field $B_0$.

FIG. 10B shows the conductors 110, 112, 124, 126 oriented perpendicular to the main magnetic field $B_0$. FIG. 10B shows that the coil remains sensitive even when the main magnetic field $B_0$ is not aligned with the direction of the conductors 110, 112, 124, 126.

It will be appreciated that, if desired, additional numbers of pairs of conductors, generally, equally spaced from each other, much the same way the two conductors of FIG. 6, and the four conductors of FIGS. 8 and 9 are spaced, may be employed. For example, if desired, a total of three pairs of conductors; each embedded within the dielectric and equally spaced from each other in a circumferential sense, might be employed. An advantage of the use of more conductors in the coil is the further improvement in sensitivity around the coil and enhanced independence of the sensitivity on coil orientation. A disadvantage is the increased minimum width or diameter of the coil that is achievable with a large number of conductive elements.

Figure 11:
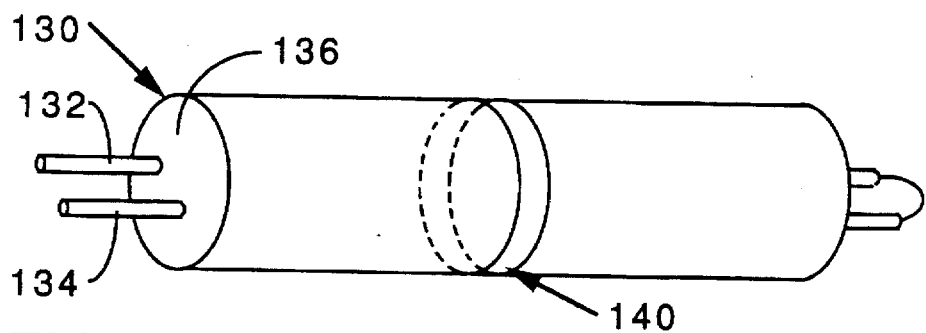
FIG. 11 is a schematic illustration of the sensitivity volume of a coil, such as that of FIG. 2 of the present invention.
Figure 12:
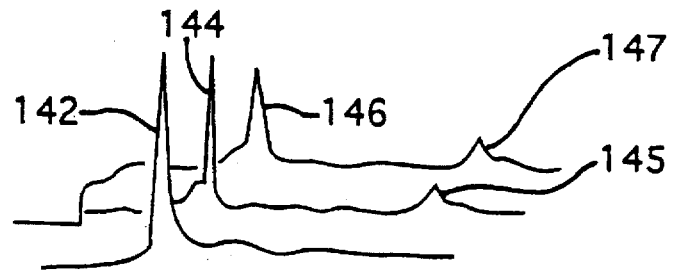
FIG. 12 is a representation of the spectra of three adjacent voxels along the length of the catheter coil of FIG. 11.

Referring to FIG. 11, there is shown a coil 130 generally of the type shown in FIGS. 2 and 3 with conductors 132, 134 being generally parallel and passing through a dielectric 136. The coil may be employed to provide a set of spatially resolved chemical shift spectra. As the sensitivity of the coil is restricted to regions close to coil conductors (see FIGS. 6 and 10), one-dimensional chemical shift imaging or 1-D spectroscopy may be employed without localization pulses. The imaging voxel, such as 140, depicted here as a cylindrical as shown in FIG. 11, is actually the shape of the sensitivity profiles shown in FIGS. 6A–6C for a two-conductor coil or in FIGS. 10A–10B for the four-conductor coil. A TR of 2000, 140 mm FOV and 64 phase encoding steps along the coil with 2 NEX was used in another experiment in which the body coil was employed to transmit RF pulses and the catheter coil employed to receive the same. The spectra of three adjacent voxels is shown in FIG. 12 with peaks 142, 144, 146 representing water signals from the three regions and peaks 145, 147 and peaks 145, 147 from lipid signals in or adjacent to the vessel walls. The bandwidth was 1000 Hz, with 1,024 point resolution, and the z dimension of the voxel 140 is 2.2 mm. The radial dimension of the voxel is determined by the sensitivity of the coil. Water and lipid peaks will tend to vary between normal and atherosclerotic vessels. As the spectra of the three adjacent voxels represented in FIG. 12 are the result of the phase of coil sensitivity above the coil and under the coil, opposing each other, some signal cancellation results.

While in the first embodiment of the invention, the coil of the present invention was employed solely as a receiver of magnetic resonance signals emanating from the specimen, in another embodiment of the invention, employing the same coil with certain modifications, if desired, the coil may serve both as an RF transmitter and as an RF receiver. In such an approach, the system would function essentially as before, in both imaging and 1-D spectroscopy, except the source of the MR excitation RF magnetic field would be the coil rather than transmitter coil in the standard MR scanner. If this approach is taken, the transmitter power may be introduced at the diode 80 of FIG. 5A with the preamplifier 82 connected to the same point by a cable tuned to be of a length $\lambda/4$ at the MR frequency.

Figure 13:
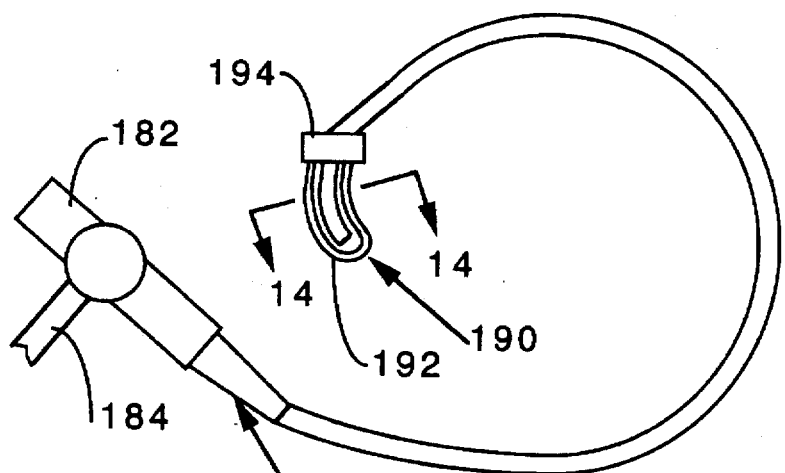
FIG. 13 is a schematic illustration of a coil of the present invention secured to an endoscope.
Figure 14:
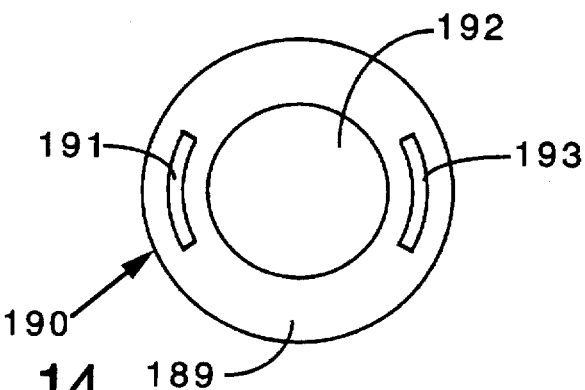
FIG. 14 is a cross-sectional illustration through 14—14 of the endoscope of FIG. 13.
Figure 15:
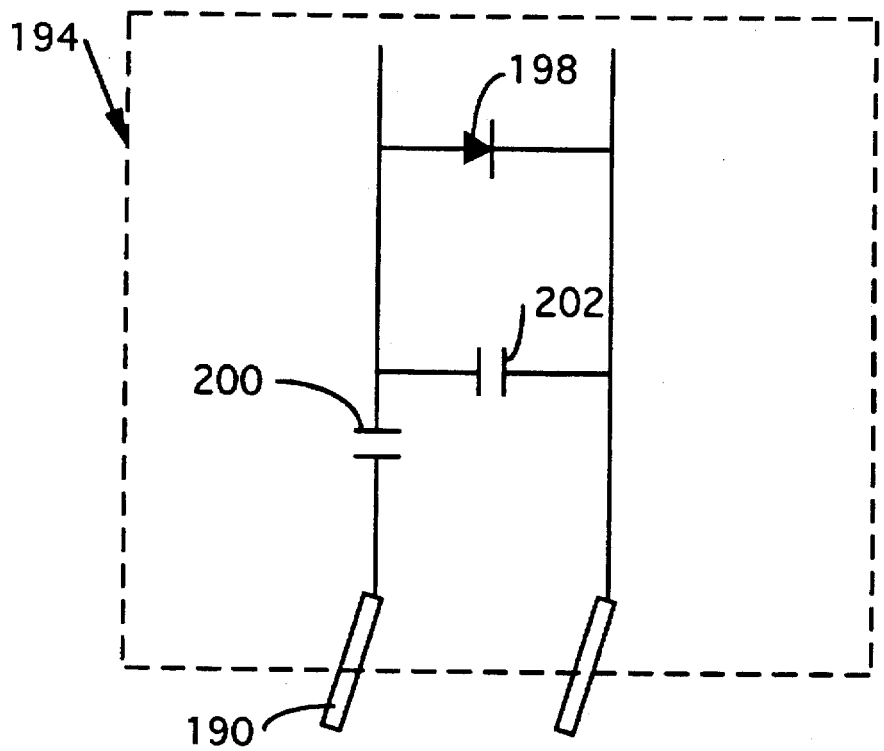
FIG. 15 illustrates a form of tuning and matching circuit for the endoscope of FIG. 13.

Referring to FIGS. 13 through 15, the coil of the present invention may be mounted on a conventional flexible endoscope 180 which has conventional external tubular connections 182, 184. The coil 190 may be fixedly secured about the circumference of the lower portion 192 of the endoscopic tube with an adjacent tuning/matching circuit 194 provided. As shown in FIG. 14, the coil 190 is of annular configuration and surrounds the lower portion 192 of the endoscope 180 which lower portion 192 is composed of an MR compatible material. The elongated coil conductors 191, 193 are embedded in annular dielectric material 189 which is intimately secured to lower end 192.

As shown in FIG. 15, the tuning/matching circuit 194 has diode 198 and capacitors 200, 202.

It will be appreciated with the present invention that the catheter coil may be employed, for example, in a blood vessel to provide an image and 1-D spectroscopic analysis of plaque built up on the interior of the vessel wall with multislice imaging being provided in an efficient manner due to the long coil being employed. It may be employed to examine many other characteristics, such as fatty streaks, calcification, sclerosis, and thrombosis, for example. It will be appreciated that substantially simultaneously with the use of the coil and the catheter, medical intervention as, for example, by laser destruction of the undesired plaque, may be employed. Similarly, any normal diagnostic or therapeutic measures undertaken with the aid of endoscope 180, may be accomplished substantially simultaneously with the use of the coil for imaging and/or spectroscopic analysis.

Figure 16:
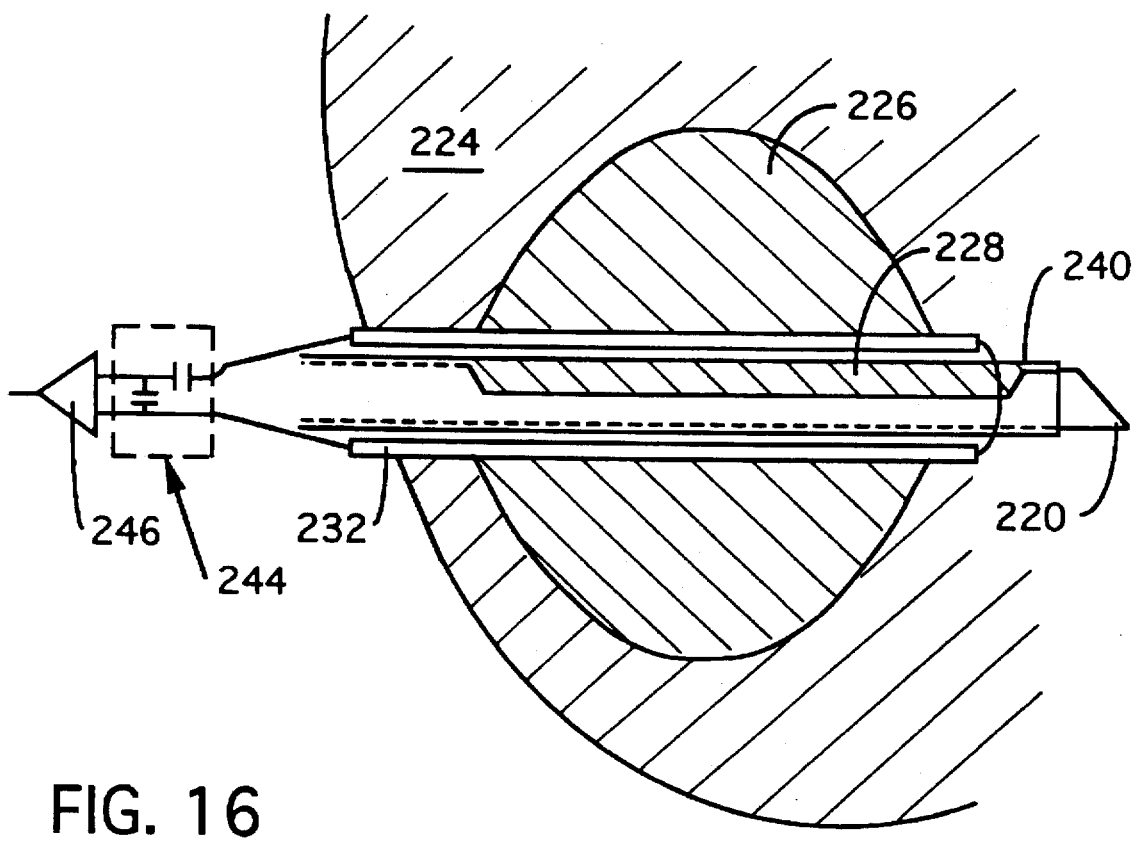
FIG. 16 is a schematic cross-sectional illustration showing the coil of the present invention employed with a biopsy needle.

Referring again to FIG. 16, there is shown the use of the invention in connection with biopsy needle 220 which is composed of a material which is magnetic resonance compatible, such as a ceramic material as distinguished from a steel material, for example. In this embodiment, the specimen 224 contains a lesion 226 from which a sample 228 has been obtained by the biopsy needle. The coil 232, which is fixedly secured to the exterior of the needle sheath 240 may be a two or four conductor coil having the general configuration shown in FIG. 14, for example. The tuning and matching circuit 244 is electrically connected to both the coil 232 and a preamplifier 246 which serves to amplify the signal before it enters the computer (not shown) for further processing. In this embodiment, the coil 232 need not be flexible and the apparatus need not enter a natural passageway within the patient. The coil may be secured to the needle by a suitable glue or resin or in the case of a ceramic needle, by depositing the conductor onto the ceramic by methods well known to those skilled in the art of electronic integrated circuit fabrication. The conductors are then sheathed with insulating material.

Figure 17A:
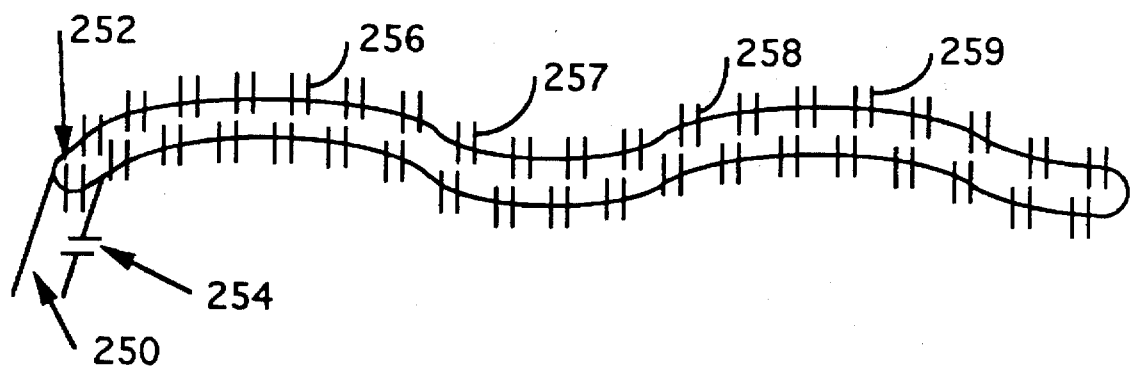
FIG. 17A illustrates a form of capacitive tuning arrangement of the present invention.
Figure 17B:
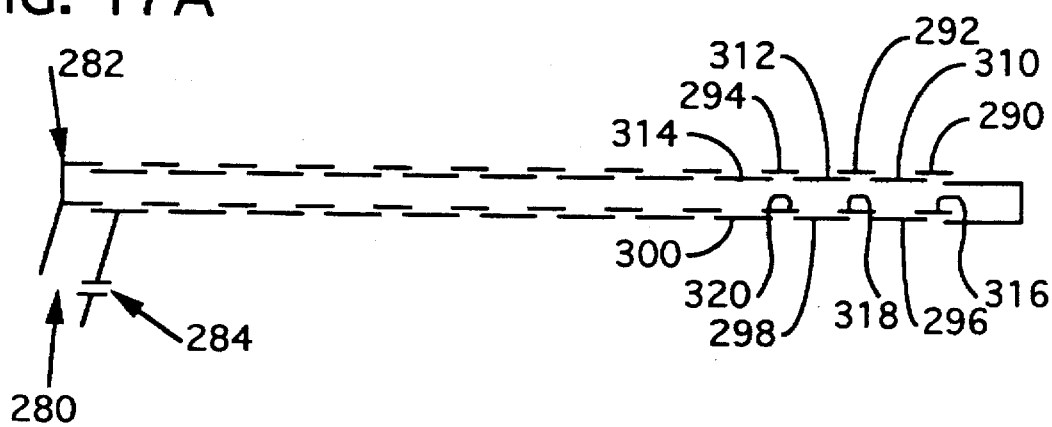
FIG. 17B illustrates an embodiment of the invention wherein distributed capacitance is employed in connection with a two conductor coil.

Referring to FIGS. 17A and 17B, another approach to reduce the dielectric losses is to distribute the tuning capacitance as distributed series capacitance along the length of the catheter coil. For example, instead of short-circuiting the two conductors, as shown in FIG. 2, by conductor 32, a tiny chip capacitor having a capacitance selected such that in combination with tuning capacitors C1 and C2 of FIG. 5, the coil is correctly tuned to the MR frequency. Other approaches will be considered with respect to the embodiments illustrated in FIGS. 17A through 21D. Considering FIG. 17A wherein the output end 250 of coil 252 has an impedance matching capacitor 254, a plurality of capacitors, such as capacitors 256, 257, 258, 259, for example, spaced throughout the longitudinal extent of the coil 252, with individual values chosen so that the coil is tuned to resonate at the MR frequency of the nuclei of interest. For example, if "f" is the MR resonance frequency, the coil may be tuned to resonate at f by allowing the values of the capacitors 256, 257, etc., each to be substantially equal to a value $C_i$, and adjusting $C_i$ such that the condition $f=(2\pi\sqrt{[LC_i/n]})^{-1}$ is met, where "L" is the coil inductance with the coil in the specimen, and n is the number of capacitors distributed along the length of the coil. The capacitors are connected by flexible conducting elements 266, 267, 268, 269, etc., with spacing "d" substantially constant along the length of the coil, as in FIG. 3. This embodiment has the advantage over that depicted in FIG. 5, that in order to meet the tuning condition for a particular value of "f," the values of $C_i$ will generally be much larger than those of $C_1$–$C_7$ in FIG. 5 and also, be sufficiently large so as to minimize dielectric losses that result from interactions between coil conductor elements 266, 267, 268, 269, etc., and the specimen. The distributed capacitance of this embodiment of the invention may be achieved by a number of means including (a) the use of discrete circuit capacitive elements of sufficiently small dimensions to meet the desired aforementioned dimensional specifications of the coil, and (13) by direct deposition of conductor onto a flexible dielectric substrate that forms the body of the coil, or (c) by etching away of conductor from a flexible dielectric substrate using techniques well known in the manufacture of printed circuit boards and integrate electronic circuit devices. An embodiment that is electrically equivalent to FIG. 17A that provides a distributed capacitance coil by method (b) is depicted in FIG. 17B. Considering FIG. 17B, wherein the output end 280 of coil 282 has an impedance matching capacitor 284, a plurality of capacitors formed by conductive elements 290, 292, 294 and where they are proximal to conductive elements 310, 312, 314, for example, are spaced throughout the longitudinal extent of the coil 282 and a plurality of capacitors formed by conductive elements 296, 298, 300 in close proximity to conductive elements 316, 318, 320, for example. The remaining unnumbered conductive elements will similarly provide a plurality of capacitors. Here, the capacitors formed by conductor 290, 292, 294 in proximity to conductors 310, 312, 314, etc., may be fabricated by deposition or etching of conducting material on two sides of a flexible dielectric substrate material such that sections 290, 292, 294 are on one side of the dielectric material and sections 310, 312, 314, etc., are on the other side. It will be appreciated that adjacent pairs of the conductive plates will provide the two conductors which form a capacitor and in the aggregate provide a plurality of capacitors along the coil. With reference to the conductors numbered for purposes of example, conductors 294 and 314 cooperate to form a capacitor as do conductors 294 and 3 12. In this manner, the capacitance is distributed along the coil and yet the coil preserves its desired flexibility.

Figure 18:
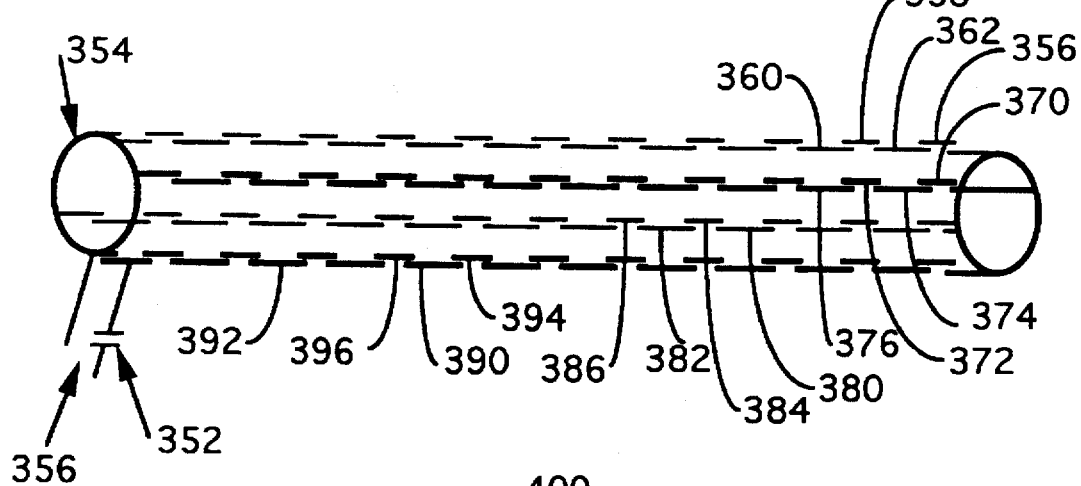
FIG. 18 is a schematic illustration of a distributed capacitance coil wherein two pairs of conductors are employed.
Figure 19:
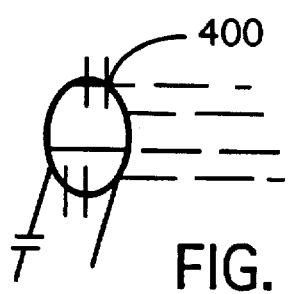
FIG. 19 is an alternate form of distributed capacitance wherein a plurality of axially spaced rings are employed as the capacitive elements.

FIG. 18 shows a similar construction wherein the output 356 and impedance matching capacitor 352 are employed in a construction wherein four conductors are used as in FIGS. 8 and 9. The coil 354 has a plurality of capacitors, such as is formed by flexible conductive elements 356, 358 and underlying flexible conductive elements 360, 362 associated with a first conductor and a plurality of capacitors formed by elements 370, 372, for example, associated with flexible elements 374, 376. On a third conductor, a series of capacitors formed by elements 380, 382 are associated with flexible conductive elements 384, 386. Finally, the fourth conductor has a plurality of capacitors, such as are formed by elements 390, 392 which are associated with flexible elements 394, 396. As an alternative to the capacitors shown in FIG. 18, a plurality of ring-shaped capacitors, such as 400, axially spaced along the coil may be employed in a coil as shown in FIG. 19.

Figure 20:
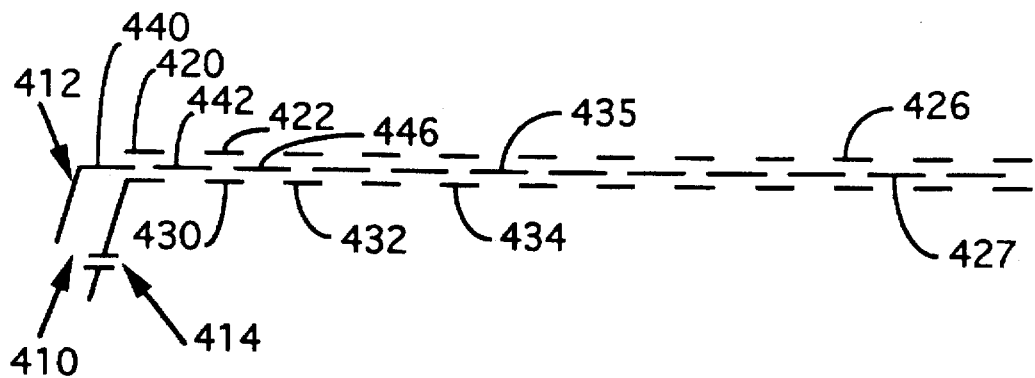
FIG. 20 is a schematic illustration of a two conductor distributed capacitance coil having a common ground.

A further embodiment of the distributed capacitance concept is shown in FIG. 20 wherein the output end 410 of coil 412 has an impedance matching capacitor 414 and a plurality of first capacitors formed by conductive elements 420, 422, 426, in association with conductive elements 440, 442, 446, 427, for example, and a plurality of second capacitors formed by conductive elements 430, 432, 434, for example, associated with the common capacitance rail 440, 442, 446, 435.

If desired, once the dielectric losses have been decreased, for example by distributing the capacitance, the catheter RF receiver coil length can be increased to increase coverage on the coil. In addition, a coil fabricated from lengths of conductor incorporating capacitance distributed at a particular value of capacitance per unit length, for example, by etching or deposition as discussed hereinbefore, can be turned to different specific MR frequencies by adjusting coil length. If the coil length is increased to λ/4 where λ is the wavelength in the coil with the coil disposed within the specimen at the MR frequencies, the coil will self-resonate and additional resonance tuning capacitors may be eliminated.

Figure 21A:
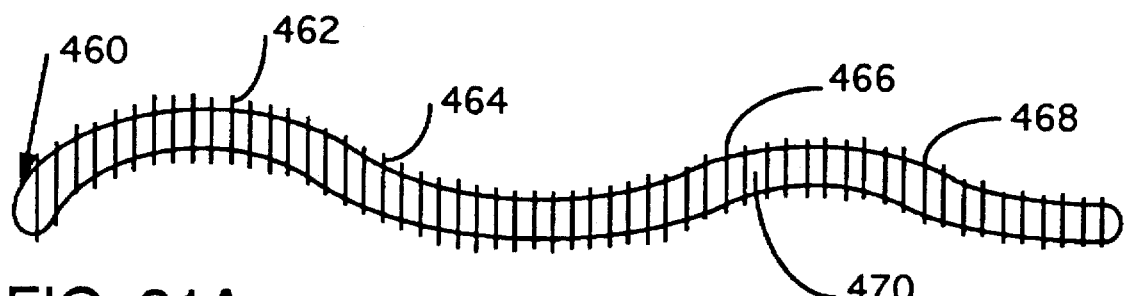
FIG. 21A illustrates schematically an alternate form of Faraday shield employing short lengths of electrical conductor.
Figures 21B, 21C, 21D:
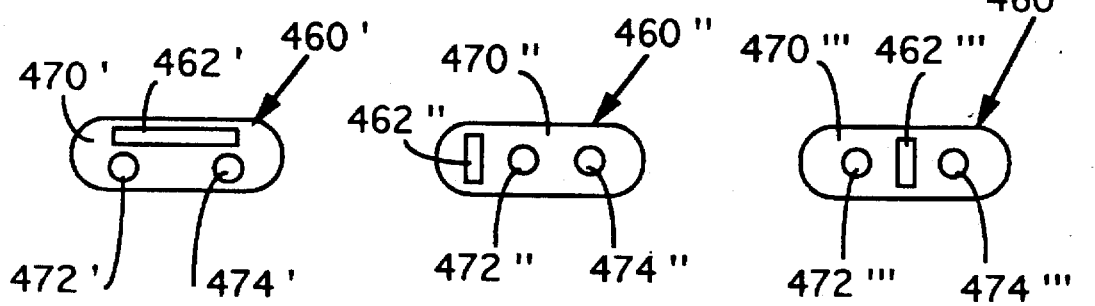
FIG. 21B–21D show cross-sectional views of several specific approaches to the embodiment of FIG. 21A.

Referring to FIGS. 7 and 21, an alternate version of Faraday shield is shown in FIG. 21A, wherein a coil 460, in lieu of having ring-like conductors, has a plurality of short length conductors 462, 464, 466, 468, for example, embedded in a flexible substrate 470 oriented substantially perpendicular to at least one pair of elongated electrical conductors that form the basic receiver coil. Examples of specific approaches to the embodiment of FIG. 21A are provided in FIGS. 21B–21D. As shown in FIG. 21B, dielectric 470' has as conductors 472' and 474' with a plurality of elongated conductors 462' positioned generally parallel to a plane passing through the conductors 472' and 474' and embedded within dielectric 470'. A plurality of such conductive elements are spaced axially along the coil. In FIG. 21C, conductors 472", 474" are positioned within dielectric 470" and the elongated conductive elements, such as 462" are oriented generally perpendicular to a plane passed through conductors 472", 474". In FIG. 21D, the elongated conductor 462''' are positioned generally perpendicular to a plane passed through conductors 472''', 474''' and is positioned between such conductors 472''', 474''' with all of the conductors being disposed within dielectric 470'''.

Figure 22:
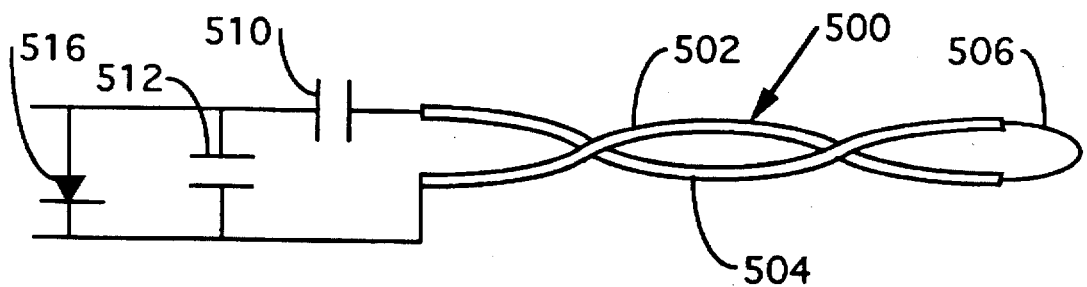
FIG. 22 represents a twisted pair coil of the present invention.

Referring to FIG. 22, there is shown a two conductor coil 500 having two conductors 502, 504 associated therewith and an electrical conductor 506 connecting the same. Associated capacitors 510, 512, which comprise the tuning/matching circuit and the diode 516, are electrically connected to the coil 500. An advantage of this embodiment of the invention, wherein the conductors 502, 504 would be encased in a suitable dielectric (not shown), is the sensitivity to the far field will drop. The number of turns per unit length of the coil 500, may be adjusted as to provide the same near field sensitivity and, thereby, improve the signal-to-noise ratio. The preferred number of rams per centimeter of length is about 1 to 2 turns.

Figure 23:
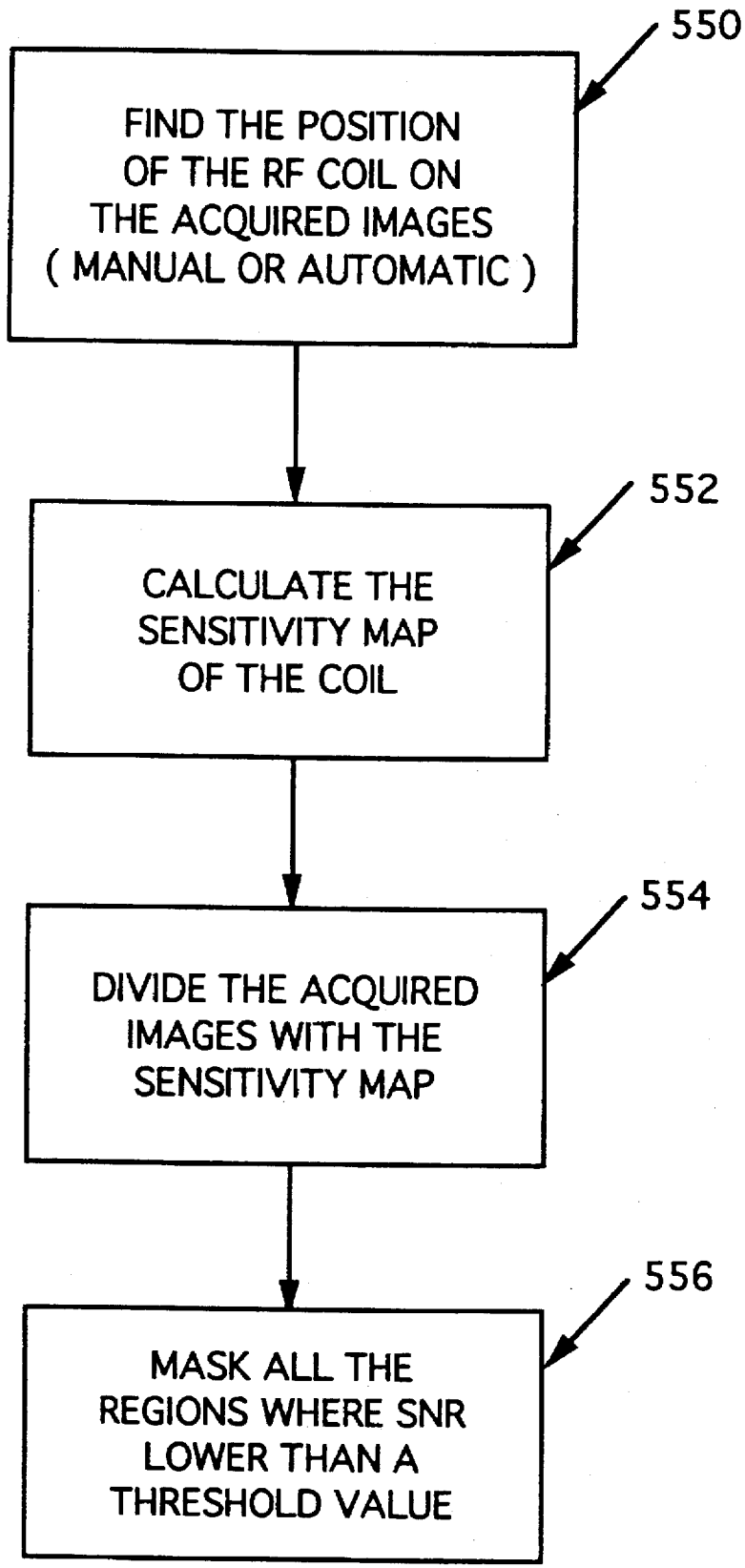
FIG. 23 is a schematic flow diagram showing a method of correcting signal variation by the sensitivity map related to the coils of the present invention.

Referring to FIG. 23, a feature of the software of the present invention will be considered. As noted hereinbefore, the RF sensitivity of the coil roughly drops by 1/r, wherein "r" equals the radial distance to the center of the coil. Although the signal-to-noise ratio is high, the dynamic range for the visualization of the signal is so high it is desirable to provide an image processing technique in order to facilitate display of all existing information. In one such approach the image is divided pixel by pixel by the sensitivity map. For reasons where the sensitivity is low, i.e, the signal is comparable or lower than the noise level, a value of 0 is assigned to the corresponding pixel. After this process, unlike the usual MR images, noise will be space dependent.

As shown in FIG. 23, first the position of the RF coil in the image needs to be determined (step 550) for sensitivity map registration purposes. This may be done either manually or automatically by a computer, for example. To minimize or completely eliminate user interaction, this can be accomplished by finding two dark spots near the pixel with the highest signal intensity. Locating the coil position, with respect to the main magnetic field, should be determined in order to calculate the sensitivity map of the coil (step 552). This can be automated by tracking the coil position in a multislice acquisition or assuming that the image plane is always perpendicular to the coil. One then divides the acquired images with the sensitivity map (step 554). Step 556 involves masking or filling the regions of the image with zero where the SNR is lower than a threshold value which is typically within the range of 1 to 5. This processing corrects the RF field inhomogeneity of the acquired image data.

It will be appreciated, therefore, that the present invention provides an improved method and associated apparatus for enhanced MR imaging and 1-D chemical shift analysis of the interior of a specimen. This is true even in situations where a tortuous path in a blood vessel requires that the receiver coil be flexible and multislice data acquisition is desired. The system also functions effectively by providing desired sensitivity to the MR signal even in oblique positions. Further, the coil provides uniform sensitivity along the coil and, as a result of the use of longer coils, facilitates a longer portion of the specimen being imaged with one coil position. Further, no tuning is required after insertion of the coil into a specimen. In a preferred embodiment, one or more pairs of conductors are embedded within a dielectric material which is flexible so as to facilitate desired bending of the same in providing images and spectroscopic analysis. The coil, in addition to serving solely as a receiver coil in one embodiment, may in another embodiment function as a transmitter coil and a receiver coil. The invention may be employed generally simultaneously with medical intervention, such as, for example, laser removal of blood vessel plaque.

The invention also contemplates enhanced efficiency through the use of a at least one of the following features: a tuning/matching circuit; a decoupling circuit; a Faraday shield; as well as distributed capacitance along the length of the coil; self-resonance; and a twisted pair coil.

While for clarity of disclosure reference has been made herein to display means for displaying an image, it will be appreciated that the image information may be stored, printed on hard copy, be computer modified, or be combined with other data. All such processing shall be deemed to fall within the terms "display" or "displaying" as employed herein.

Whereas particular embodiments of the present invention have been described herein for purposes of illustration, it will be appreciated by those skilled in the art that numerous variations of the details may be made without departing from the invention as described in the appended claims.

We claim:

1. A method of internal magnetic resonance analysis of a specimen comprising positioning said specimen within a main magnetic field, introducing an invasive probe having an elongated receiver coil into said specimen, employing as said receiver coil a resiliently flexible coil having at least one pair of elongated electrical conductors disposed within a resiliently flexible dielectric material and having a pair of ends electrically connected to each other, maintaining the spacing between said pair of elongated electrical conductors substantially uniform throughout said analysis, imposing said main magnetic field on region of interest of said specimen, applying RF pulses to said region of interest to excite magnetic resonance signals within said specimen, applying gradient magnetic pulses to said region of interest to spatially encode the magnetic resonance signals, said receiver coil receiving said magnetic resonance signals and emitting responsive output signals, processing means for receiving and processing said output signals and converting them into MR information, and employing display means for receiving MR information from said processing means and displaying the same as an image or as chemical shift spectra.

2. The method of claim 1 including employing in said coil said conductors which are generally parallel to each other.

3. The method of claim 2 including including in said receiver output signals spatially localized chemical shift information, employing said processing means to convert said chemical shift information into chemical shift spectra, and employing said display means to receive and display said chemical shift spectra.

4. The method of claim 3 including employing said method in one-dimensional chemical shift imaging, wherein said chemical shift information is spatially resolved in a direction substantially along the length of said receiver coil at the region of interest in said specimen.

5. The method of claim 2 including employing said processing means to convert said receiver coil output signals into image information, and employing said display means to receive and display said image information.

6. The method of claim 2 including employing as said receiver coil a coil having a conductor length measured along the portion of said conductor thereof disposed within said dielectric material of about 2 cm to 50 cm.

7. The method of claim 6 including employing as said coil a coil having a length of about 5 cm to 20 cm.

8. The method of claim 7 including employing as said coil a coil having a maximum width of about 0.5 mm to 15 mm.

9. The method of claim 6 including employing as said coil a coil having a maximum width of about 0.5 mm to 2 cm.

10. The method of claim 6 including employing as said coil a coil having substantially uniform sensitivity along the coil.

11. The method of claim 2 including delivering said receiver coil within said probe which is a catheter, into a blood vessel.

12. The method of claim 11 including inserting said coil containing catheter within veins to image and acquire MR chemical shift information about atherosclerotic plaques.

13. The method of claim 12 including employing said method generally simultaneous with plaque removal from said blood vessel.

14. The method of claim 12 including employing as said coil a coil which remains sensitive to magnetic resonance signals even at oblique positions.

15. The method of claim 14 including said coil having the length measured along one leg thereof within said dielectric material of about 2 cm to 50 cm, and a maximum width of about 0.5 mm to 2 cm.

16. The method of claim 2 including employing as a said receiver coil a coil having two said pairs of electrical conductors embedded in a dielectric material with conductors within said pair being electrically connected to each other.

17. The method of claim 2 including employing a decoupling circuit disposed intermediate said receiver coil and said processing means to resist current induction during said RF pulses.

18. The method of claim 2 including employing a Faraday shield around said receiver coil to resist undesired dielectric losses.

19. The method of claim 18 including employing as said Faraday shield a plurality of electrically conductive ting-like elements secured to the dielectric material of said coil in relatively axially spaced position from adjacent said ting-like elements.

20. The method of claim 18 including employing as said Faraday shield a plurality of elongated electrically conductive elements secured to said dielectric material.

21. The method of claim 2 including employing said coil as an RF pulse transmitting source in addition to said employment as a receiver coil.

22. The method of claim 2 including securing said receiver coil to said invasive probe, wherein said invasive probe is an endoscope.

23. The method of claim 2 including securing said receiver coil to the exterior of said invasive probe, wherein said invasive probe is a magnetic resonance compatible biopsy needle.

24. The method of claim 2 including employing said method in vitro on a specimen which has been removed from a patient.

25. The method of claim 2 including employing said method in vivo on a patient.

26. The method of claim 25 including employing said process on a human being.

27. The method of claim 26 including employing said method in a natural opening in said human being.

28. The method of claim 2 including employing a tuning/matching circuit electrically interposed between said receiver coil and said processing means to enhance RF power transfer and MR signal-to-noise ratio from said receiver coil, and performing said analysis without adjusting said tuning/matching circuit immediately prior to probe introduction into said specimen or during the period said receiver coil is in said specimen.

29. The method of claim 28 including employing as said tuning/matching circuit a plurality of capacitors of fixed capacitance.

30. The method of claim 2 including employing a plurality of capacitors relatively spaced along said receiver coil and secured to a flexible substrate thereof.

31. The method of claim 30 including electrically connecting said capacitors to a common capacitance rail.

32. The method of claim 30 including tuning said receiver coil by altering the length thereof.

33. The method of claim 30 including establishing said plurality of capacitors by providing a plurality of relatively spaced electrically conductive elements each of which cooperate with another of said elements to function as a capacitor.

34. The method of claim 30 including creating said plurality of capacitors by etching an electrical conductor which was previously secured to a dielectric substrate.

35. The method of claim 34 including employing as said dielectric substrate a flexible material.

36. The method of claim 30 including creating said plurality of capacitors by depositing electrically conductive material on a flexible dielectric material.

37. The method of claim 2 including employing said coil in multislice imaging of said specimen without requiring movement of said receiver coil.

38. The method of claim 2 including employing computer means as said processing means.

39. The method of claim 1 including said electrical conductors in said coil being helically intertwined with each other, whereby induction of undesired eddy currents is resisted.

40. The method of claim 1 including employing a patient as said specimen, and performing generally simultaneously with said imaging a medical procedure on said patient.

41. The method of claim 1 including locating the coil position with respect to said main magnetic field by said processing means, calculating by said computer means the sensitivity map of said coil, and employing said sensitivity map to enhance the display of the acquired images.

42. Magnetic resonance specimen analysis apparatus comprising magnetic field generating means for establishing a main magnetic field on said specimen, magnetic field gradient generating means for establishing gradients in said main magnetic field, RF signal generating means for emitting pulsed RF signals to at least portions of said specimen disposed within said main magnetic field, an elongated receiver coil having at least a pair of elongated electrical conductors disposed within a dielectric material and having a pair of ends electrically connected to each other and having means for receiving signals emitted from said specimen responsive to said RF pulses and emitting responsive output signals, processing means for receiving and processing said output signals from said receiver coil and creating MR information related thereto, visual display means for displaying said MR information received from said processing means as an image or as chemical shift spectra, and probe means for positioning said receiver coil with respect to said specimen for insertion of said receiver coil into said specimen.

43. The magnetic resonance specimen imaging apparatus of claim 42 including said pair of conductors disposed generally parallel to each other.

44. The apparatus of claim 43 including said processing means having means for converting said output signals into spatially localized chemical shift spectra, and said visual display means having means for displaying said spectra.

45. The apparatus of claim 44 including said magnetic field gradient generating means has means for generating a magnetic field gradient substantially parallel to said receiver coil over a region of interest of said specimen in order to generate one-dimensional resolved chemical shift spectra that are spatially resolved substantially along the direction of the receiver coil in a region of interest in said specimen.

46. The apparatus of claim 44 including said receiver coil having a conductor length measured along the portion of said conductor disposed within said dielectric material of about 2 cm to 50 cm.

47. The apparatus of claim 46 including said receiver coil having a length of about 5 cm to 20 cm.

48. The apparatus of claim 46 including said receiver coil having a maximum width of about 0.5 mm to 2 cm.

49. The apparatus of claim 44 including said receiver coil being secured within catheter means, said catheter means having an external diameter structured to be received within the blood vessel of a patient, and said processing means having means for imaging and spectroscopically analyzing said output signals.

50. The apparatus of claim 49 including said receiver coil having a length which facilitates multislice imaging without moving said coil.

51. The apparatus of claim 44 including said receiver coil being flexible, whereby said receiver coil may assume a tortuous path upon insertion into said specimen.

52. The apparatus of claim 44 including said receiver coil being structured to remain sensitive to magnetic resonance signals even when disposed at oblique angles with respect to the main magnetic field.

53. The apparatus of claim 52 including said receiver coil having substantially uniform sensitivity along the length of said receiver coil.

54. The apparatus of claim 44 including said receiver coil having two said pairs of electrical conductors with conductors within each of said pairs being electrically connected to each other.

55. The apparatus of claim 54 including said coil having the length measured along the portion of one conductor thereof disposed within said dielectric material of about 2 cm to 50 cm, and a diameter of about 0.5 mm to 2 cm.

56. The apparatus of claim 44 including decoupling circuit means disposed intermediate said receiver coil means and said processing means to resist undesired current induction during said RF pulses.

57. The apparatus of claim 56 including a Faraday shield disposed around said receiver coil to resist undesired dielectric losses.

58. The apparatus of claim 57 including said Faraday shield including a plurality of electrically conductive ring-like elements secured to the dielectric material of said receiver coil in relatively axially spaced position from each other.

59. The apparatus of claim 57 including said Faraday shield having a plurality of elongated conductive elements secured to said dielectric material.

60. The apparatus of claim 44 including said receiver coil means having means to function as an RF pulse transmitting source to excite MR signals.

61. The apparatus of claim 44 including said probe being an endoscope, and said receiver coil being secured to the exterior thereof.

62. The apparatus of claim 44 including said probe being a magnetic resonance compatible biopsy needle, and said receiver coil being secured to the exterior of said biopsy needle.

63. The apparatus of claim 44 including said probe being structured to be received within a naturally occurring opening in a human being.

64. The apparatus of claim 44 including a tuning/matching circuit electrically interposed between said receiver coil and said processing means for enhancing RF power transfer from said receiver coil.

65. The apparatus of claim 64 including said tuning/matching circuit having capacitor means electrically connected to said receiving coil to enhance the MR signal-to-noise ratio.

66. The apparatus of claim 65 including said tuning/matching circuit having a plurality of capacitors.

67. The apparatus of claim 44 including said receiver coil having a plurality of capacitors relatively spaced along said coil and secured to a flexible substrate, whereby the presence of said capacitors will not preclude flexing of said receiver coil.

68. The magnetic apparatus of claim 67 including said capacitors being electrically connected to a common capacitance rail.

69. The apparatus of claim 67 including said coil being tunable by adjusting the length thereof.

70. The apparatus of claim 67 including said coil having as said plurality of capacitors a plurality of relatively spaced electrically conductive elements each of which cooperate with another of said elements to function as a capacitor.

71. The apparatus of claim 67 including said capacitors having a plurality of electrically conductive elements secured to a dielectric said substrate.

72. The apparatus of claim 71 including said electrically conductive elements having etched edges.

73. The apparatus of claim 67 including said plurality of spaced capacitors having a plurality of axially spaced ring shaped capacitors.

74. The apparatus of claim 42 including said electrical conductors in said receiver coil means being helically intertwined with each other, whereby said MR response signals may be enhanced.

75. The apparatus of claim 42 including said processing means having means for locating the receiver coil position with respect to said receiver main magnetic field, calculating the sensitivity map of said coil, and means for employing said sensitivity map to enhance the display of acquired images.

76. A magnetic resonance coil assembly comprising a resiliently flexible elongated receiver coil for internal magnetic resonance analysis of a region of interest of a specimen by insertion of the receiver coil into the specimen to receive magnetic energy emitted by nuclei disposed within a specimen which is positioned within a main magnetic field responsive to bursts of radio frequency energy and gradient magnetic pulses which are both applied to the specimen and emitting responsive signals, and said receiver coil having at least one pair of elongated electrically connected conductors disposed within a flexible dielectric material and having means for receiving signals emitted from a specimen and emitting responsive output signals.

77. The coil assembly of claim 76 including said coil having a plurality of capacitors spaced along said coil and secured to a flexible substrate thereof.

78. The coil assembly of claim 77 including said coil being tunable by adjusting the length thereof.

79. The coil assembly of claim 77 including said coil having as said plurality of capacitors a plurality of relatively spaced electrically conductive elements each of which cooperate with another of said elements to function as a capacitor.

80. The coil assembly of claim 77 including said capacitors having a plurality of electrically conductive elements secured to a dielectric substrate.

81. The coil assembly of claim 80 including said electrically conductive elements having etched edges.

82. The coil assembly of claim 77 including said plurality of spaced capacitors having a plurality of axially spaced ring shaped capacitors.

83. The coil assembly of claim 77 including said coil having a length disposed within said dielectric material of about 2 cm to 50 cm, and a maximum width of about 0.5 to 2 cm.

84. The coil assembly of claim 77 including said coil assembly having a fixed capacitance tuning/matching circuit operatively associated thereof electrically connected to said elongated conductors.

85. The coil assembly of claim 84 including a decoupling circuit operatively associated with said tuning/matching circuit.

* * * * *